(12) United States Patent
Ariff et al.

(10) Patent No.: US 9,683,210 B2
(45) Date of Patent: Jun. 20, 2017

(54) CELL SEPARATION APPARATUS AND METHODS OF USE

(71) Applicant: TISSUE GENESIS, LLC, Honolulu, HI (US)

(72) Inventors: Gregory D. Ariff, Herndon, VA (US); Thomas Cannon, Honolulu, HI (US); Jennifer L. Case, Alexandria, VA (US); Christian L. Haller, Alexandria, VA (US); Paul Kosnik, Honolulu, HI (US); Charles P. Luddy, Alexandria, VA (US); Craig A. Mauch, Clifton Park, NY (US); Erik Vossman, Honolulu, HI (US); Stuart K. Williams, Tucson, AZ (US)

(73) Assignee: Tissue Genesis, LLC, Honolulu, HI (US)

( * ) Notice: Subject to any disclaimer, the term of this patent is extended or adjusted under 35 U.S.C. 154(b) by 0 days.

(21) Appl. No.: 14/868,235

(22) Filed: Sep. 28, 2015

(65) Prior Publication Data

US 2016/0237396 A1 Aug. 18, 2016

Related U.S. Application Data

(60) Division of application No. 11/789,188, filed on Apr. 23, 2007, now Pat. No. 9,144,583, which is a continuation-in-part of application No. 11/314,281, filed on Dec. 22, 2005, now Pat. No. 8,202,725.

(60) Provisional application No. 60/697,954, filed on Jul. 12, 2005, provisional application No. 60/638,199, filed on Dec. 23, 2004.

(51) Int. Cl.
C12M 3/00 (2006.01)
C12M 1/00 (2006.01)
A61K 35/12 (2015.01)

(52) U.S. Cl.
CPC ............. *C12M 47/04* (2013.01); *A61K 35/12* (2013.01); *C12M 45/05* (2013.01); *C12M 45/06* (2013.01); *C12M 45/09* (2013.01)

(58) Field of Classification Search
CPC ....... C12M 21/08; C12M 45/05; C12M 45/04
See application file for complete search history.

(56) References Cited

FOREIGN PATENT DOCUMENTS

WO WO 9501419 A1 * 1/1995 ............. A61F 2/062

* cited by examiner

*Primary Examiner* — Rosanne Kosson
(74) *Attorney, Agent, or Firm* — Conley Rose, PC

(57) ABSTRACT

The present invention provides automated devices for use in supporting various cell therapies and tissue engineering methods. The present invention provides an automated cell separation apparatus capable of separating cells from a tissue sample for use in cell therapies and/or tissue engineering. The cell separation apparatus can be used in combination with complementary devices such as cell collection device and/or a sodding apparatus to support various therapies. The automated apparatus includes media and tissue dissociating chemical reservoirs, filters, a cell separator and a perfusion flow loop through a graft chamber which supports a graft substrate or other endovascular device. The present invention further provides methods for using the tissue grafts and cell samples prepared by the devices described herein in a multitude of therapies including revascularization, regeneration and reconstruction of tissues and organs, as well as treatment and prevention of diseases.

7 Claims, 21 Drawing Sheets

CELL SEPARATION APPARATUS AND METHODS OF USE

RELATED APPLICATION INFORMATION

This application claims priority and is a divisional of U.S. patent application Ser. No. 11/789,188, filed Apr. 23, 2007, entitled CELL SEPARATION APPARATUS AND METHODS OF USE, which is a continuation-in-part of U.S. patent application Ser. No. 11/314,281 filed Dec. 22, 2005, entitled CELL SODDING METHOD AND APPARATUS, which claims priority to U.S. Provisional Application No. 60/697,954 filed Jul. 12, 2005, entitled AUTOMATED CELL SODDING METHOD AND APPARATUS, and U.S. Provisional Application No. 60/638,199 filed Dec. 23, 2004 entitled CELL SODDING METHOD AND APPARATUS, each of which are incorporated herein by reference in their entirety.

FIELD OF THE INVENTION

The present invention is related to devices and methods for use in supporting various therapeutic procedures including cell therapies and tissue engineering.

BACKGROUND OF THE INVENTION

Cell therapy and tissue engineering is developing toward clinical applications for the repair and restoration of damaged or diseased tissues and organs. In particular, the development of vascular grafts is a major goal in the field of cardiac and peripheral vascular surgery. Cardiovascular disease is the leading cause of mortality and morbidity in the first world. The standard of care, the autograft, is not without serious morbidity. Patients with systemic disease, leaving no appropriate autograft material or having already undergone autografts, numbering 100,000 a year in the United States alone, have few autograft options.

Researchers have thus been studying synthetic grafts for over 30 years. A major challenge is providing graft materials that are biocompatible, i.e., nonthrombogenic, nonimmunogenic, mechanically resistant, and have acceptable wound healing and physiological responses (e.g., vasoconstriction/relaxation responses, solute transportation ability, etc.). Furthermore, tissue graft materials should be easy to handle, store and ship, and be commercially feasible.

Vessels have two principal failure modes: mechanical and biological, caused by thrombosis within the vessel and subsequent occlusion and/or cellular ingrowth. Synthetic vessels having material properties capable of withstanding arterial pressure are commonplace, making the search for non-thrombogenic materials the prime research interest. Endothelial cells obtained from the patient have been shown to decrease the thrombogenicity of implanted vessels (Williams et al., 1994, *J. Vasc. Surg.*, 19:594-604; Arts et al., 2001 *Lab Invest* 81:1461-1465).

Endothelial cells are of critical importance in establishing a non-thrombogenic cell lining within synthetic grafts. Thus, it is desirable to achieve rapid cellular adhesion in or on a permeable matrix, scaffold, or other permeable cell substrate material in a matter of minutes or hours with an instrument that lends itself to the operating room environment, maintains a sterile barrier, is easy to use, and produces consistent graft results.

Currently, there are four main approaches for meeting these requirements, but with limited success: (i) the use of decellularized tissue materials; (ii) the use of a self-assembly mechanism, wherein cells are cultured on tissue culture plastic in a medium that induces extracellular matrix (ECM) synthesis; (iii) the use of synthetic biodegradable polymers, onto which cells are subsequently seeded and cultured in a simulated physiological environment; and (iv) the use of biopolymers, such as a reconstituted type I collagen gel, which is formed and compacted with tissue cells by the application of mechanical forces to simulate a physiological environment (see, e.g., Robert T. Tranquillo, 2002, *Ann. N.Y. Acad. Sci.*, 961:251-254).

Pressure gradients involving transient high pressures have been used to deposit cells onto a permeable scaffold by a sieving action, i.e., providing a bulk flow and using a substrate or scaffold material having pores smaller than the cell population, thus capturing cells in the matrix (e.g., U.S. Pat. No. 5,628,781; Williams et al., 1992, *J Biomed Mat Res* 26:103-117; Williams et al., 1992, *J. Biomed Mat Res* 28:203-212.). These captured cells have been shown to subsequently adhere to the scaffold material, but with only limited clinical applicability due to failure to fully meet the requisites for successful grafts discussed above, i.e., biocompatibility, mechanical strength, and necessary physiological properties.

Beginning in the late 1970s, endothelial cell seeding was employed experimentally to improve the patency of small diameter, polymeric vascular grafts to counteract adverse reactions. Since that time, advances have been made toward this goal, with the majority of the focus on engineering a biological or a bio-hybrid graft.

Endothelial cells are more complex than was originally believed in that they do not merely create a single cell lining on the lumenal surface of blood vessels. Endothelial cells also release molecules that modulate coagulation, platelet aggregation, leukocyte adhesion, and vascular tone. In the absence of these cells, e.g., in the case of the lumen of an implanted synthetic polymeric vascular graft, the host reaction progresses to eventual failure. Loss of patency within the first thirty days post-implantation is due to acute thrombosis. This early stage failure is a consequence of the inherent thrombogenicity of the biomaterial's blood-contacting surface, which is non-endothelialized. To date, the only known completely non-thrombogenic material is an endothelium; any other material that comes into contact with the bloodstream is predisposed to platelet deposition and subsequent thrombosis. The long-term failure mode of small diameter polymeric vascular grafts is anastomotic hyperplasia leading to a loss of patency. The precise mechanisms behind initiation of anastomotic hyperplasia are still being defined; however, endothelial cell and smooth muscle cell dysfunctions and improper communications are likely involved.

Early workers in the field of small diameter graft development sought to promote graft endothelialization and, thereby, increase patency by transplanting a varying degree of autologous endothelial cells onto vascular grafts prior to implantation. This process has become known as endothelial cell seeding (partial coverage relying on continued cell proliferation) or cell sodding (full coverage). Seeding refers to a process which includes preclotting prosthetic surfaces with endothelial cells in platelet rich plasma (PRP). Sodding, by comparison, refers to a process which includes plating endothelial cells onto a pre-established PRP clot. Sodded graft surfaces are typically prepared utilizing a two-step procedure. First, PRP is clotted onto a graft, incubated for an effective period of time and then washed with culture media. Second, the PRP coated graft is plated with endothelial cells. In contrast, seeded graft surfaces are typically prepared using a one-step plating procedure, whereby endothelial cells suspended directly in PRP are plated onto a graft surface. Accordingly, in a sodded graft, endothelial cells are plated onto the surface of a PRP clot, whereas endothelial cells are plated within the PRP clot in a seeded graft. Rupnick, et al., 1989, *J Vascular Surgery* 9(6):788-795.

The underlying hypothesis is fairly simple; that is, by promoting the establishment of the patient's own endothelial cells on the blood contacting surface of a vascular prosthesis, a "normal" endothelial cell lining and associated basement membrane, together known as the neo-intima, will form on the graft and counteract the rheologic, physiologic, and biomaterial forces working synergistically to promote graft failure. After 30 years of research in this area, including promising animal data, this simple hypothesis has not yet yielded a clinical device.

The failure modes with endothelial-seeded grafts have been identical to untreated polymeric grafts, namely thrombosis and intimal hyperplasia. The failure modes, at least partially, are linked to the lack of a functional endothelial layer, neo-intima, on the lumenal surface of the graft and/or abnormal endothelial and smooth muscle cell direct and indirect communication. These failures in early human trials came despite successful demonstrations of seeded grafts developing into a cell lining development. These data show that neo-intimal formation on polymeric vascular graft lumenal surfaces in animal models occurs by endothelial cell proliferation from perianastomotic arteries, the microvessels of graft interstices, or circulating progenitor endothelial cells not strictly from the seeded cells.

A potential source for endothelial cell seeding is microvascular endothelial cells (MVEC). Williams et al. pioneered both freshly isolated and cultured human, canine, rabbit, rat, bovine and pig endothelial cells, specifically MVEC, in their laboratory to study cellular function. The source for human MVEC was aspirated tissue from cosmetic liposuction. Two separate protocols for human fat MVEC isolation were used depending on the end use of the cell population. The protocols differed in isolation complexity from a simple, operating room-compatible procedure for immediate sodding of human or animal grafts to a more elaborate procedure if the MVEC will be subsequently cultured.

The isolation of human MVEC has been enhanced by the use of liposuction to obtain samples of human fat. The process of aspirating fat through a liposuction cannula dissociates subcutaneous fat into small pieces which boosts the efficacy of the digestion process. The fat may be digested with collagenase (4 mg/cc) for 20 minutes, at 37° C. which releases >$10^6$ cells per gram of fat. These MVEC can be separated from the fat by gradient centrifugation. The MVEC will form a pellet and can subsequently be resuspended in culture medium after discarding the supernatant. These cells have undergone routine characterization to determine the cellular makeup of the primary isolates. A majority of the cells isolated via this procedure are endothelial cells due to their expression of von Willebrand antigen, lack of expression of mesothelial cell specific cytokeratins, synthesis of angiotensin converting enzyme, prostacyclin and prostaglandin E2, synthesis of basement membrane collagens and the morphologic expression of micropinocytic vesicles.

A human clinical trial was undertaken to evaluate endothelial cell transplantation in patients requiring peripheral bypass. During the trial, large quantities of endothelial cells were placed directly on the lumenal surface of an ePTFE graft. To improve cell deposition, all grafts were pre-wetted in culture medium containing autologous serum. Cells were suspended in the same medium at a density of $2 \times 10^5$ cells/cm$^2$ graft lumenal area. This solution was held at a cross-wall, or transmural, pressure gradient of 5 psi to force cells onto the surface, a process termed pressure sodding. After institutional approval, 11 patients were enrolled and received the experimental graft. During surgical prep, the patients underwent liposuction to remove approximately 50 grams of abdominal wall fat. The fat was processed using the aforementioned procedure and the resulting cell population was pressure sodded on the intended graft and immediately implanted. After more than 4 years of follow-up, these grafts have maintained a patency rate similar to that of saphenous vein grafts.

Pressure gradients involving transient (<1 min.) relatively high pressures (250 mmHg) have previously been used to deposit cells onto a permeable scaffold by a sieving action, i.e., providing a bulk flow and using a substrate or scaffold material having pores smaller than the cell population, thus capturing cells in the matrix (e.g., U.S. Pat. No. 5,628,781; Williams et al., 1992, J Biomed Mat Res 26:103-117; Williams et al., J Biomed Mat Res 28:203-212.) However, despite the aforementioned advances, clinical coronary applicability has been limited to date because the vessels do not maintain sufficiently cohesive non-thrombogenic surfaces; research has focused on additional maturation time in vitro.

Endothelial cells are of critical importance in establishing a non-thrombogenic cell lining. In addition, a need still exists for an efficient and reliable method for producing endothelial cell linings on a synthetic graft in an operating room setting, and the current invention provides a solution. It is desirable to achieve rapid cell adhesion in or on a permeable matrix, scaffold or other permeable cell substrate material in a matter of minutes or hours with an instrument that lends itself to the operating room environment, maintains a sterile barrier, is easy to use, produces consistent graft results, and is inexpensive. The present invention enables the isolation of large quantities of endothelial cells from fat tissue and the rapid cell sodding of synthetic grafts, and enables automation and adhesion of cells in a turn-key, operating room-ready instrument for the rapid sodding of the graft. This invention will likely have other applications in addition to the lining of grafts for implantation.

SUMMARY OF THE INVENTION

The present invention provides devices for use in supporting various cell therapies and tissue engineering methods. Specifically, the present invention provides a cell separation apparatus capable of rinsing and separating cells from a tissue sample for use in cell therapies and/or tissue engineering. In a particular embodiment of the invention, the cell separation apparatus can be used in combination with a sodding apparatus to support autologous endothelialization of vascular grafts and endovascular devices.

In one embodiment, the cell separation apparatus comprising a media reservoir; a cell processing device comprising at least one inlet and at least one outlet, a first lobe and a second lobe, at least one pump, and at least one valve adapted to divert or prevent fluid flow, all of which are in fluid communication with one another. In a preferred embodiment, the cell processing device comprises a centrifuge. In another embodiment the cell processing device is disposable. In additional embodiments, the cell processing device further comprises an extraction tube and/or a rotating coupling. In a particular embodiment, the rotating coupling further comprises a pressurized spray nozzle.

In another embodiment, the cell separation system of the present invention is designed to be modular such that components may be re-used in other systems developed by the inventors. In an embodiment, the cell separation device is adapted for use with a cell sodding device and/or a cell harvesting device. In an embodiment, the apparatus is fully automated and may comprise, for example, a human machine interface, an electronic graphical display, sensors, alarms, a cell counting device, and bar code reading device. In additional embodiments, the apparatus may comprise a heater, a waste reservoir, or a tissue dissociating chemical reservoir. In a specific embodiment, the cell separation apparatus is a handheld device.

In other embodiments, the apparatus may include one or more filters, for example, between the cell processing device inlet and the tissue dissociating chemical reservoir; or between an outlet of the cell processing device and a sterile cell collection device. In one embodiment, the filter excludes particles greater than about 100 microns, and in another embodiment, the filter excludes particles greater than 30 microns. In a specific embodiment, the sterile cell collection device is a syringe.

The media used in the present invention may be M199, M199E, PBS, Saline, and Di-Cation Free DPBS. In a preferred embodiment, the media is M199E. In another embodiment, the tissue dissociating chemical is collagenase.

A kit is also provided for use in a cell therapy comprising the cell separation apparatus of the present invention adapted for use with a cell sodding apparatus, wherein the cell separation apparatus and cell sodding apparatus are contained within a durable enclosure. In one embodiment, the kit comprises a flow path cartridge comprising one or more fluid reservoirs, at least one inlet and at least one outlet; a cell processing cartridge having at least one inlet and at least one outlet; an optional graft chamber cartridge for holding a graft substrate, the graft chamber cartridge having at least one inlet and at least one outlet; at least one pump configured to cause flow through a flow path; at least one valve configured to direct flow from the cell separator cartridge to the graft chamber cartridge; where the flow path cartridge, cell separator cartridge and graft chamber cartridge communicate to form a continuous flow path, and wherein said flow path cartridge, cell separator cartridge, and optional graft chamber cartridge communicate with a modular kit enclosure capable of providing power to the apparatus.

In one embodiment, the flow path cartridge, cell processing cartridge and graft chamber cartridge are disposable. In another embodiment, the cell processing cartridge comprises a centrifuge. The apparatus of the claimed invention can also be adapted for use with a cell macerator which is in communication with the flow path cartridge.

In another embodiment of the present invention, the kit enclosure comprises at least one sensor means for detecting the presence of the flow path cartridge, the cell processing cartridge and the graft chamber, and or at least one sensor means for monitoring and controlling temperature, pressure and flow rate, wherein the sensor means is in communication with an alarm.

Methods for preparing a tissue graft using the apparatus of the present invention are also provided in which media containing adherent cells is introduced into the graft chamber, and a sustained low pressure transmural flow of the media across the substrate for a time period sufficient to adhere the cells to the substrate is applied. In a particular embodiment the adherent cells are microvascular endothelial cells derived from adipose tissue. In another embodiment the endothelial cells are harvested from a patient to be treated with the apparatus of the present invention.

Additionally, methods for regenerating a tissue or organ in a subject by injecting into the tissue or organ a cell suspension prepared by the apparatus of the invention are also provided. Methods for treating a wound and preventing adhesion formation in a tissue or organ of a subject in need thereof by injecting into the tissue or organ at least one cell suspension prepared by the apparatus of the invention are also provided.

The present invention also provides an automated, sterile and safe method and devices to form cells on a suitable graft for clinical use in a short period of time, as well as methods and devices for collecting a sample of cells suitable for therapeutic use. The present invention further provides methods for using the tissue grafts and cell samples prepared by the devices described herein in a multitude of therapies including revascularization, regeneration and reconstruction of tissues and organs as well as treatment and prevention of diseases.

DETAILED DESCRIPTION OF THE INVENTION

Figure 1:
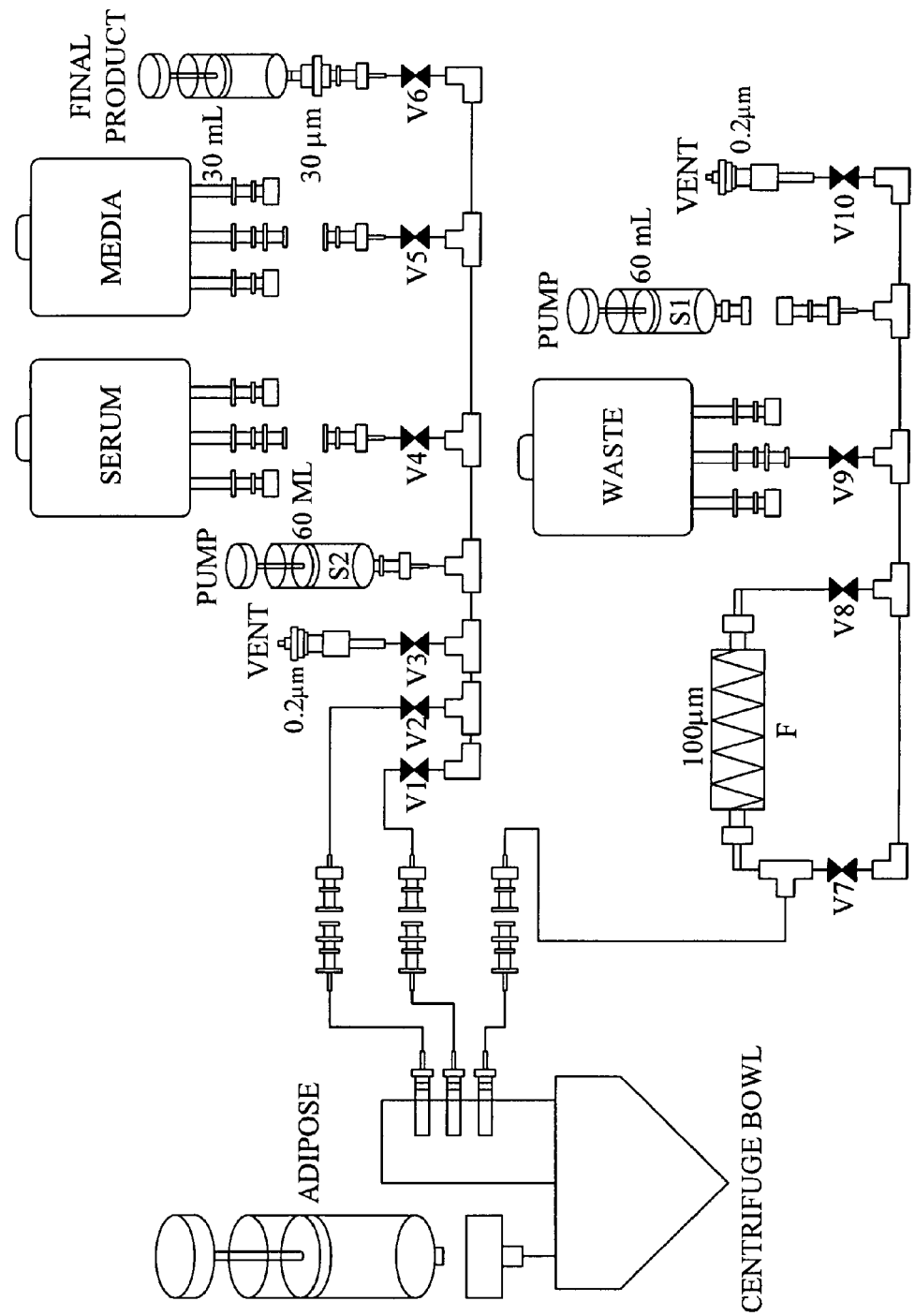
FIG. 1 is a schematic illustrating the system flow path of an embodiment of the cell separation apparatus.

Embodiments of the present invention are described herein in the context of devices for use in supporting various cell therapies and tissue engineering methods. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In accordance with the present disclosure, the components and process steps described herein may be implemented using various types of operating systems, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

The present invention provides devices for use in supporting various cell therapies and tissue engineering methods. Cell therapy, cellular therapy, or cell-based therapy refers to the use of human or animal cells to replace or repair diseased or damaged tissue and/or cells, or to treat or prevent a disease or disorder.

Specifically, the present invention provides a cell separation apparatus capable of digesting, rinsing, and separating cells from a tissue sample for use in cell therapies and/or tissue engineering. As used herein, "cell rinsing" refers to the process of using additional fluid to resuspend cells that have been isolated from the fat/collagenase mixture. The resuspended cells can then undergo a second isolation process via centrifugation to purify the cell product (MVECs). This rinsing process reduces the concentration of digestion byproducts such as, e.g., red blood cells, collagenase and proteins.

In a particular embodiment of the invention, the cell separation apparatus can be used in combination with a sodding apparatus to support autologous endothelialization of vascular grafts.

Cell Separation Apparatus

Figure 3A:
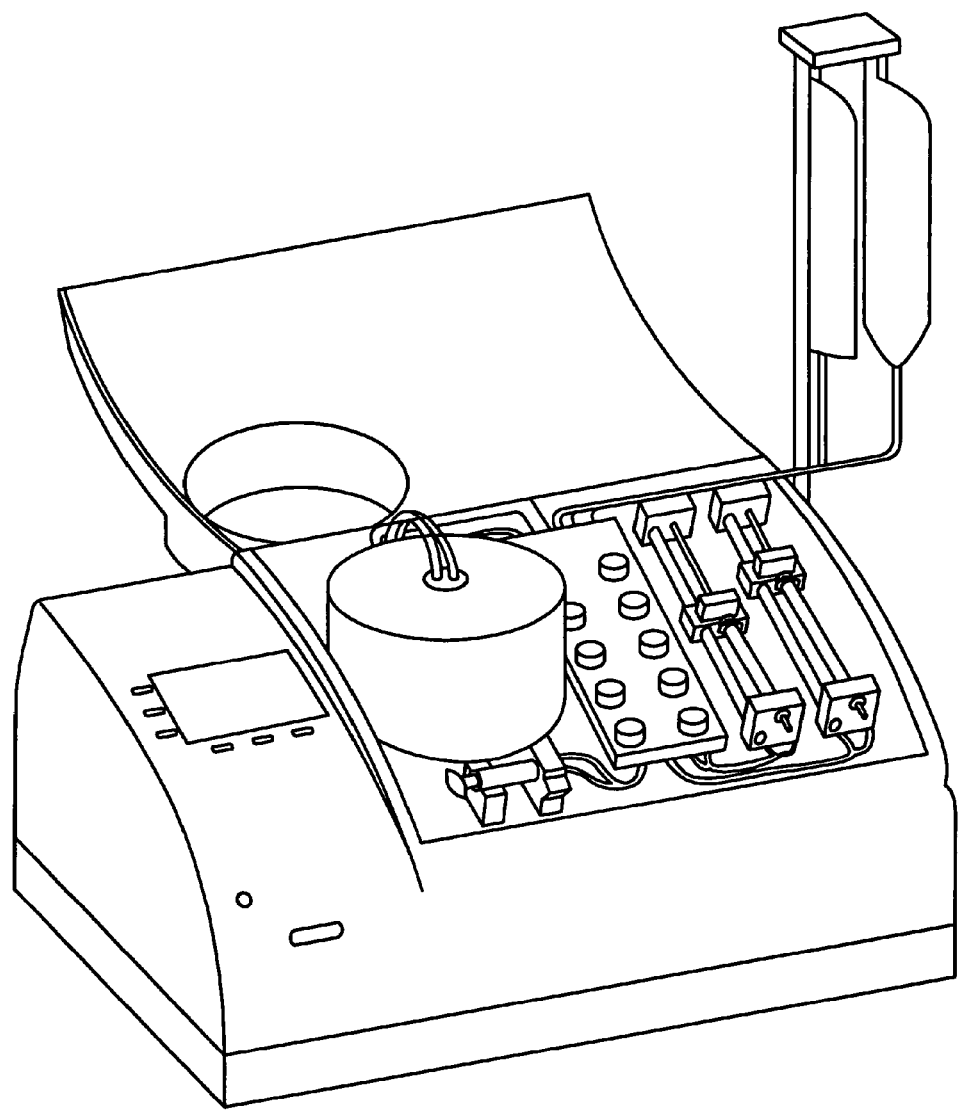
FIG. 3(A) provides a perspective views in accordance with one embodiment of the cell separation apparatus of the present invention including the human-machine interface, the cell processing device (centrifuge), tube cassette, media bags, syringe pumps, pinch valves, collection syringe and barcode scanner; (B) provides a perspective view of the cell separation apparatus of accordance with another embodiment of the present invention; and (C) provides a view of the rear of the cell separation apparatus in accordance with one embodiment of the present invention.
Figure 3B:
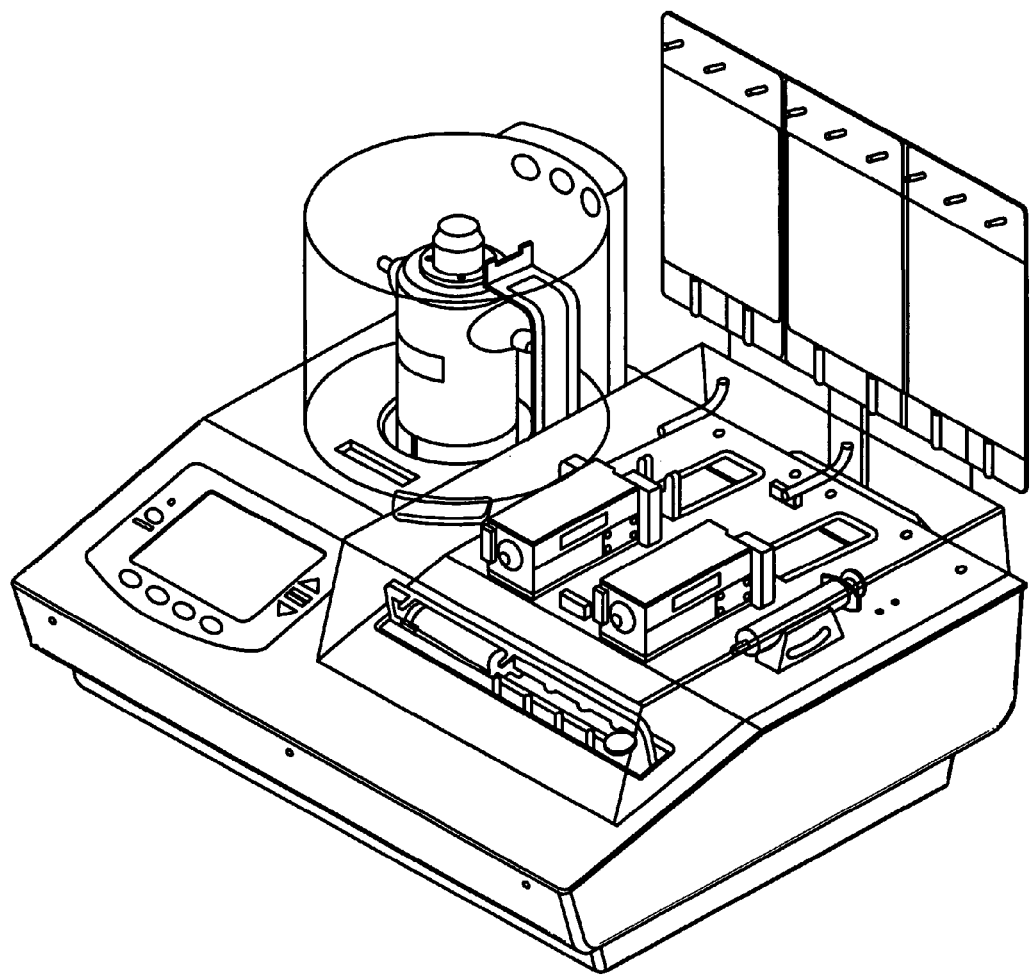
Figure 3C:
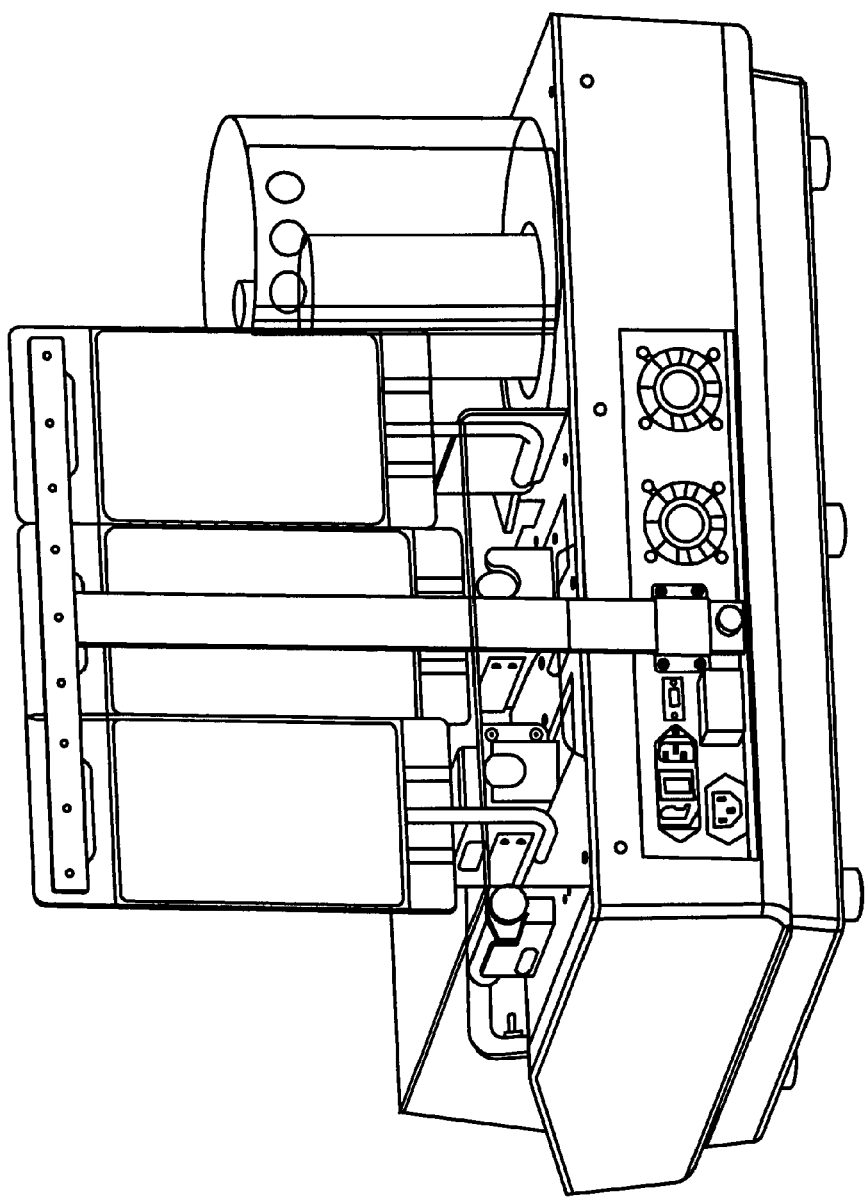

In one embodiment of the present invention, the cell separation module or cell separation apparatus is a stand-alone piece of equipment that contains all necessary electronics and components to cut, heat, digest, and separate adipose tissue. In a preferred embodiment, the cell separation component comprises a centrifuge. An outlet from the cell separation module supplies a single cell suspension of isolated cells, to be connected to either the graft sodding module, cell collection module, or other module. FIG. 3 shows the cell separation module durable and disposable components including the human-machine interface, cell processing device (centrifuge), tube cassette, media bags, syringe pumps pinch valves, collection syringe and barcode scanner.

In one embodiment, the cell separation module durable unit houses all of the electronics necessary for operation of the device, including the computer boards, software, power supply, and an user interface. In a preferred embodiment, the user interface includes an LCD screen with buttons that guides the user through the set-up and operation of the device. The cell separation module durable can also house the necessary pinch valves, motors, sensors and other durables required for cutting, heating, digesting, and centrifuging the subject tissue. In a preferred embodiment, the subject tissue is adipose tissue. Pinch valves protrude from the enclosure on a top flat surface to allow valves to engage the disposable fluid pathway. In a preferred embodiment, electronics are located a maximum distance from any fluid pathways.

In another embodiment, the device includes a mountable hook to hang media and waste bags. Preferably, the bag hook is mounted to either the graft sodding durable or the cell collection durable to maximize the distance between the media bags and electronics housed in the cell separation durable. This separation reduces risk of electronics damage from fluid spills.

In a particular embodiment of the invention, all elements of the cell separation module flow path are disposable. In one embodiment, these disposable components can be assembled on a rigid tray that loads onto the cell separation module durable. The user loads the disposable tray by placing the tray onto the flat surface of the durable by aligning the pinch valves with the valve cutouts in the disposable tray. The user then slides the tray forward to engage tubing loops in the pinch valves and lock the disposable tray in place. All disposable components are located in the tray to align with and engage the necessary durable components in the cell separation durable by this loading operation. The tray design minimizes the user's burden for set-up and disposal by eliminating the need for many tubing connections and individual loading of many disposable components. After loading the tray, the user can load the disposable centrifuge bowl into a recess provided in the durable component and attach inlet and outlet tubing from the disposable tray to the centrifuge, media bag, waste bag, and sodding or collection unit.

The fluid path (flow path) schematic for the cell processing apparatus, including the interaction between the centrifuge bowl of the cell processing apparatus and the fluid path, is shown in FIG. 1. The centrifuge bowl of the cell processing apparatus and fluid path is shown in FIG. 2.

The fluid tubing matrix, bags of fluid (e.g., PBS and/or Serum), a waste bag and the syringe for S2 are loaded into the Cell Separation Unit. These items along with the Centrifuge Bowl and Rotating Coupling comprise the consumables for the device. In an embodiment, the valves of FIG. 1 are pinch valves and block flow by pinching the tubing within the tubing matrix. FIG. 10(A)-(D) depicts a pinch valve manifold rack in accordance with one embodiment of the present invention. Preferably, the valves are part of the durable instrument and do not contact the fluid directly. In one embodiment, the device is designed to hold and process about 60 ml of adipose tissue and 60 ml of collagenase solution.

Figure 2A:
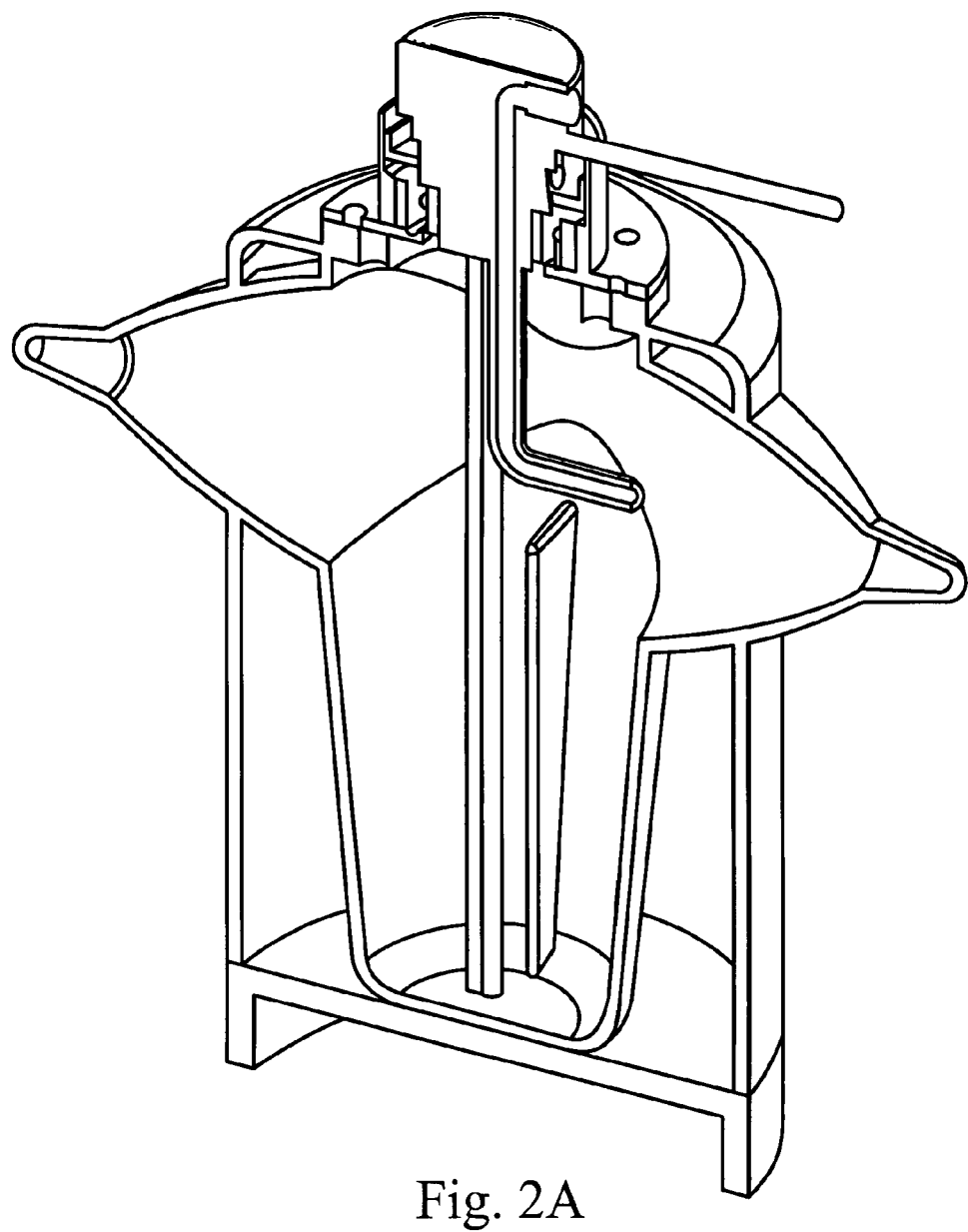
FIG. 2(A) depicts a cross section of the processing device of the cell separation apparatus including the spray nozzle member and inner and outer centrifuge bowls in accordance with one embodiment of the present invention; (B) provides a perspective view of the cell processing apparatus in accordance with one embodiment of the present invention; and (C)-(F) depicts the twist locking mechanism which joins the processing device to the cell separation apparatus in accordance with one embodiment of the present invention.
Figure 2B:
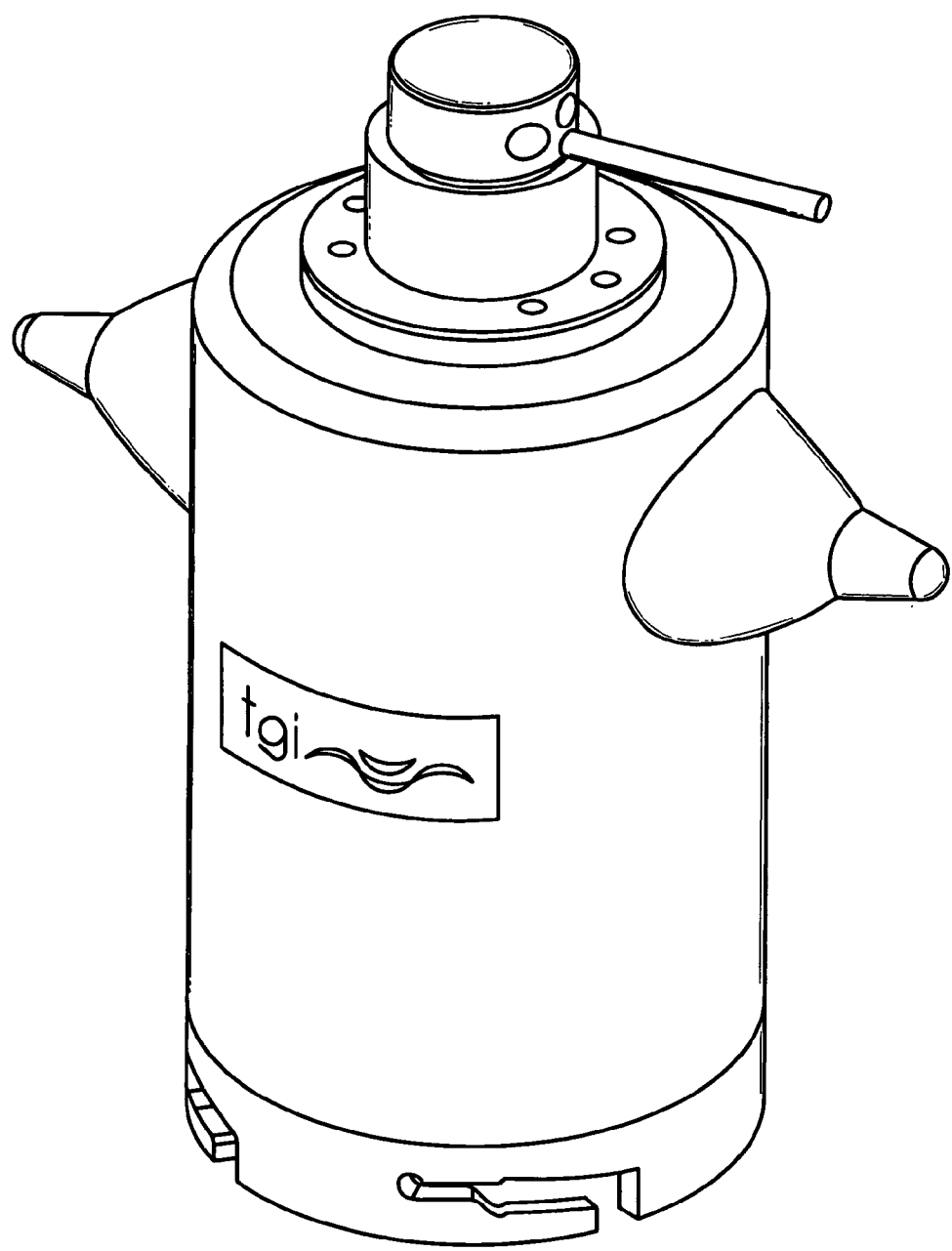
Figure 2C:
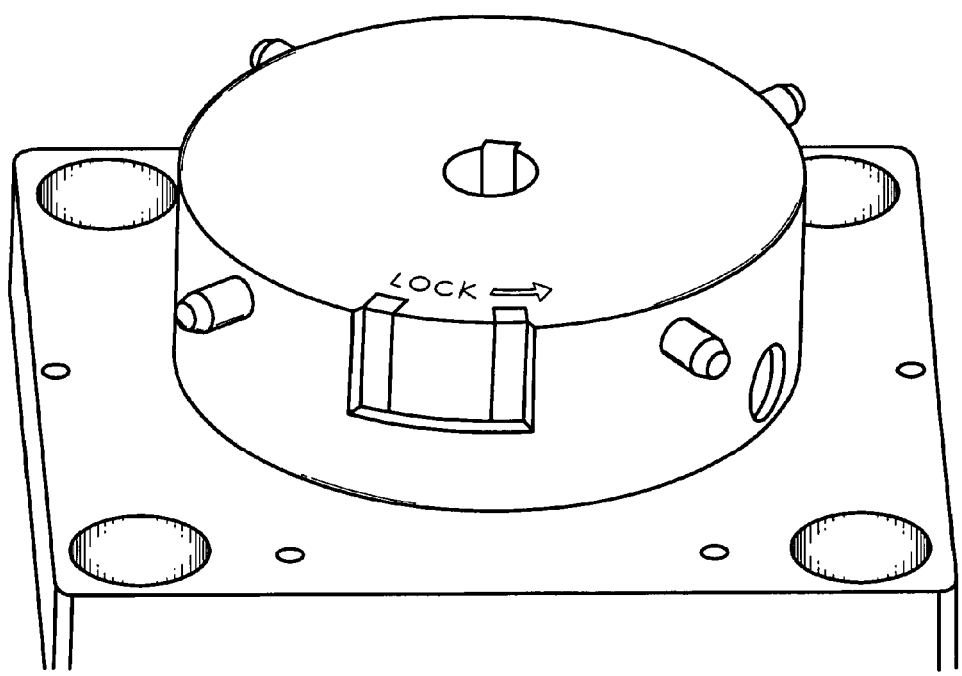
Figure 2D:
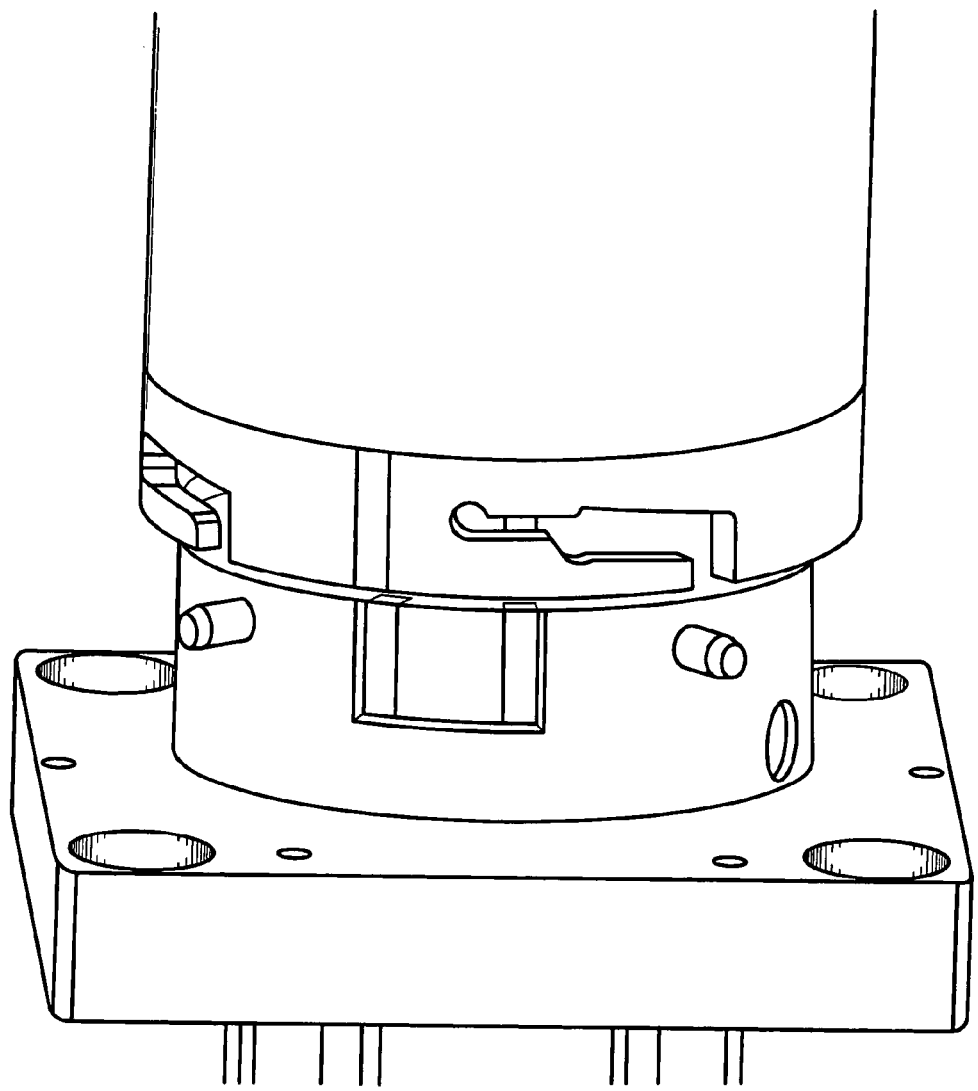
Figure 2E:
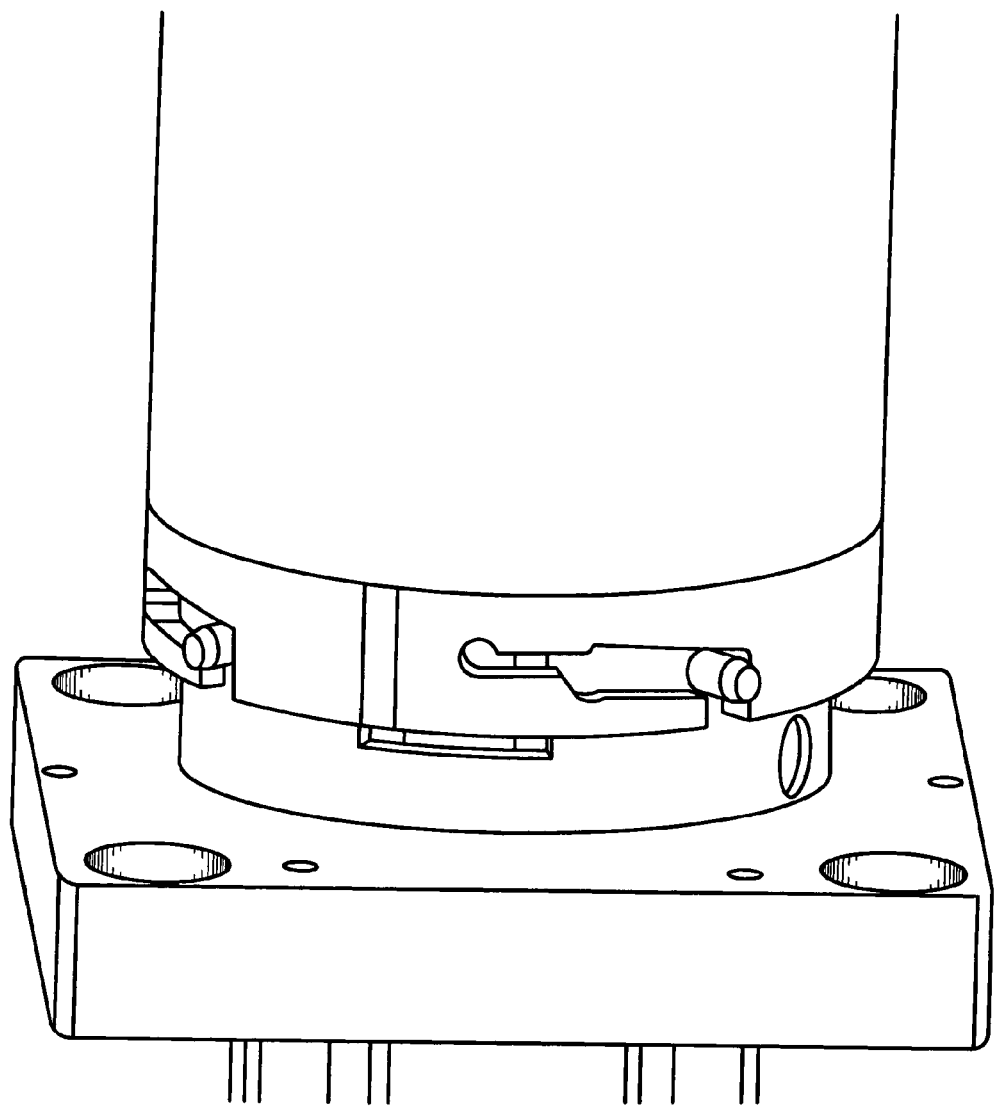
Figure 2F:
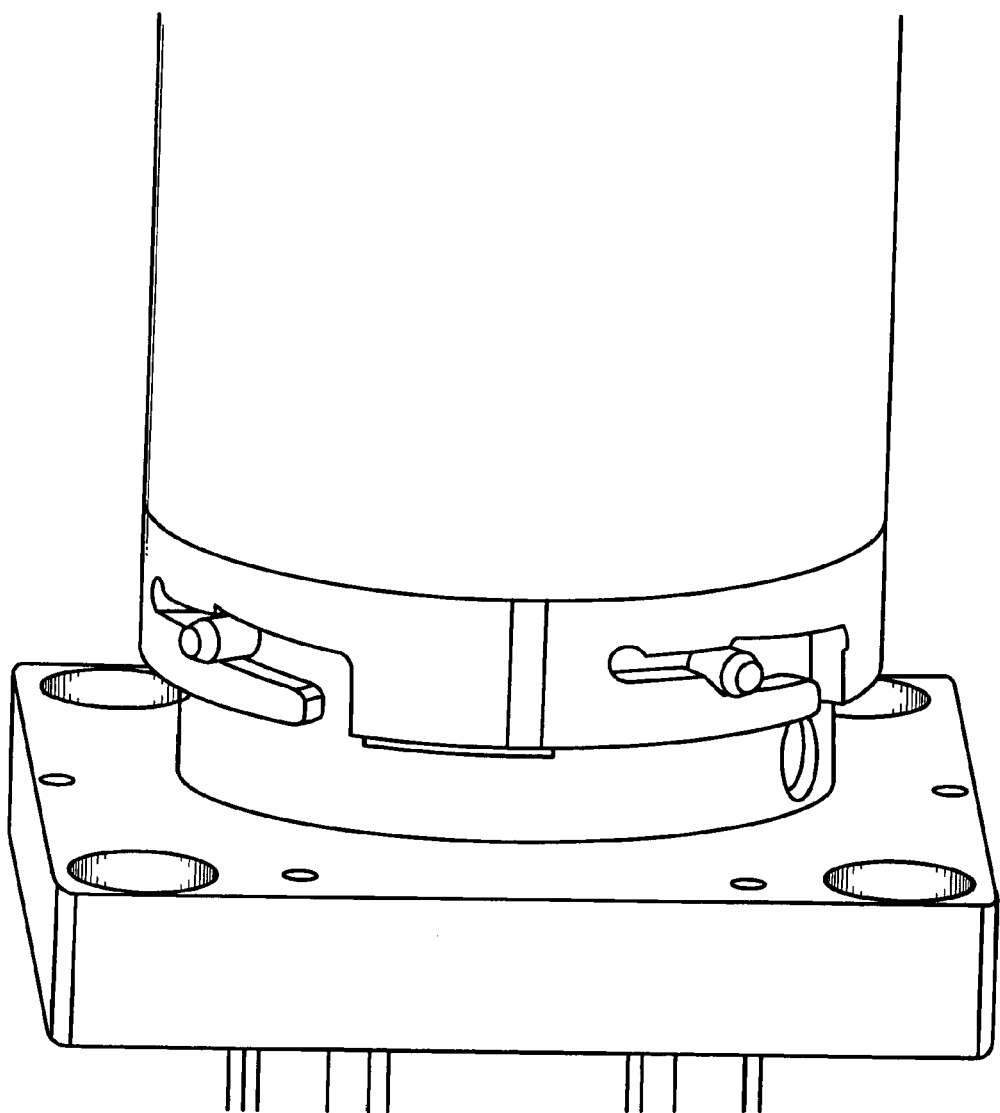
Figure 9A:
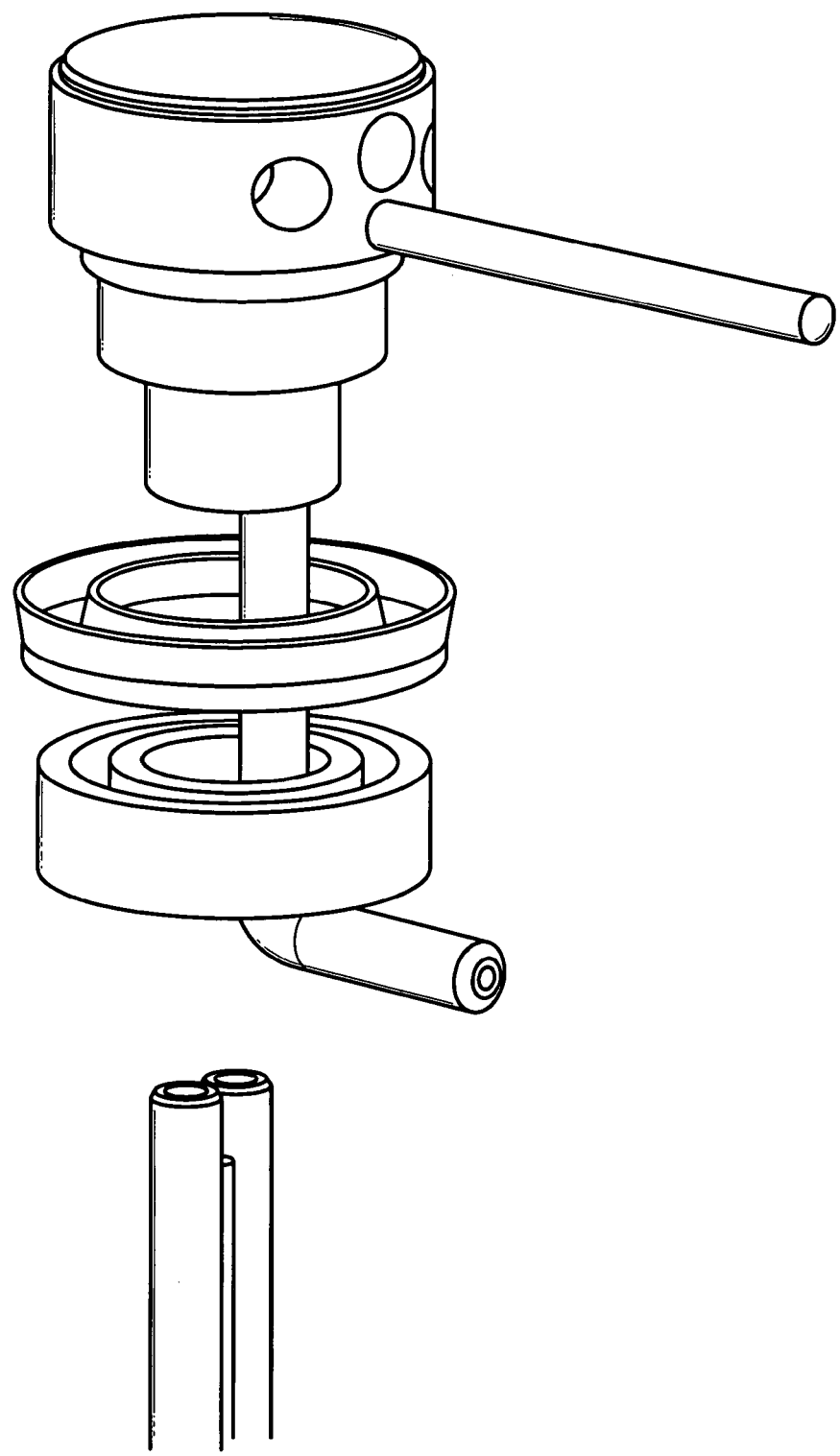
FIG. 9(A) depicts a jet spray nozzle and rotating coupling in accordance with one embodiment of the present invention; and (B) depicts a spray nozzle member aligned with one lobe of the centrifuge bowl in accordance with one embodiment of the present invention.
Figure 9B:
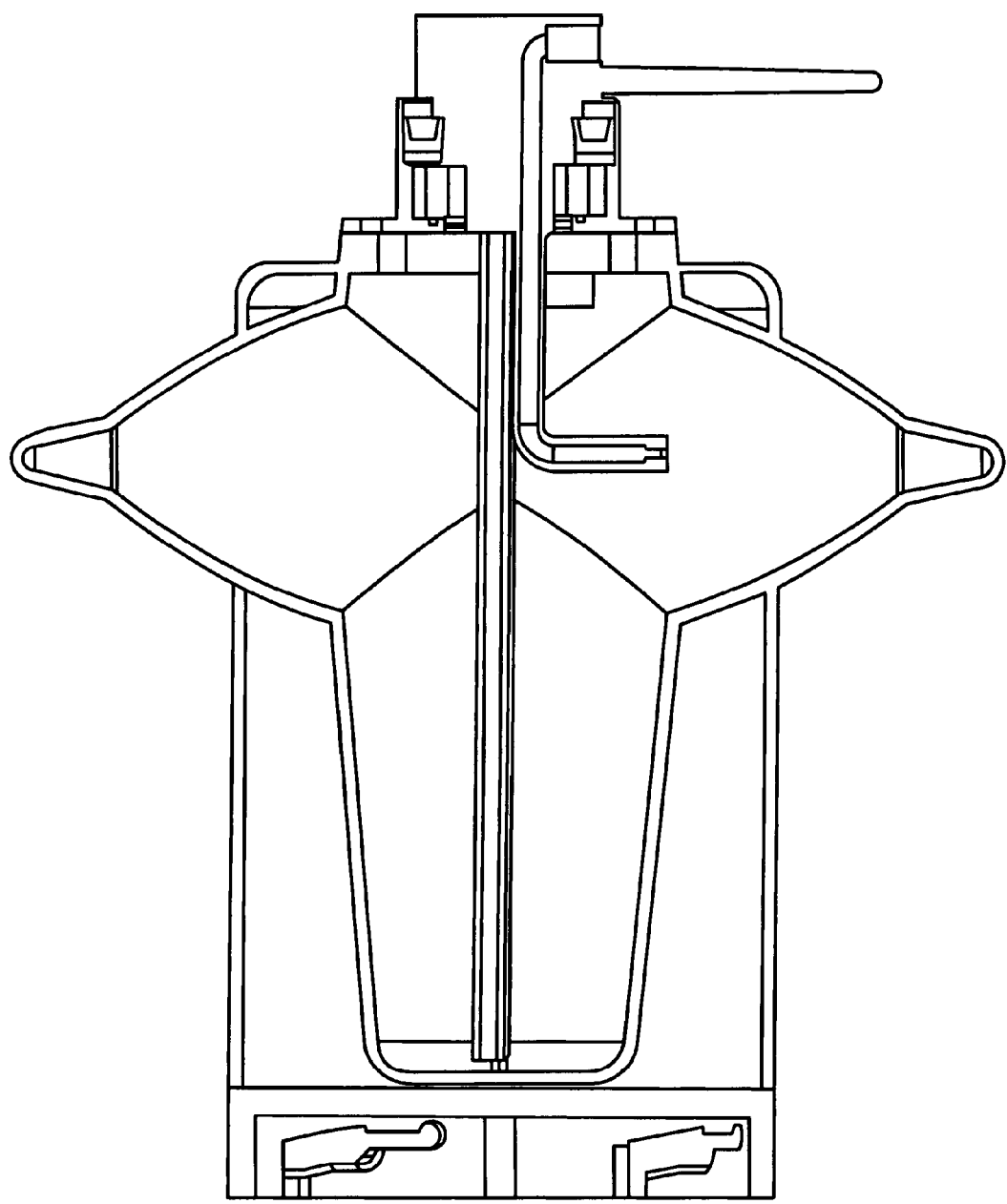
Figure 10A:
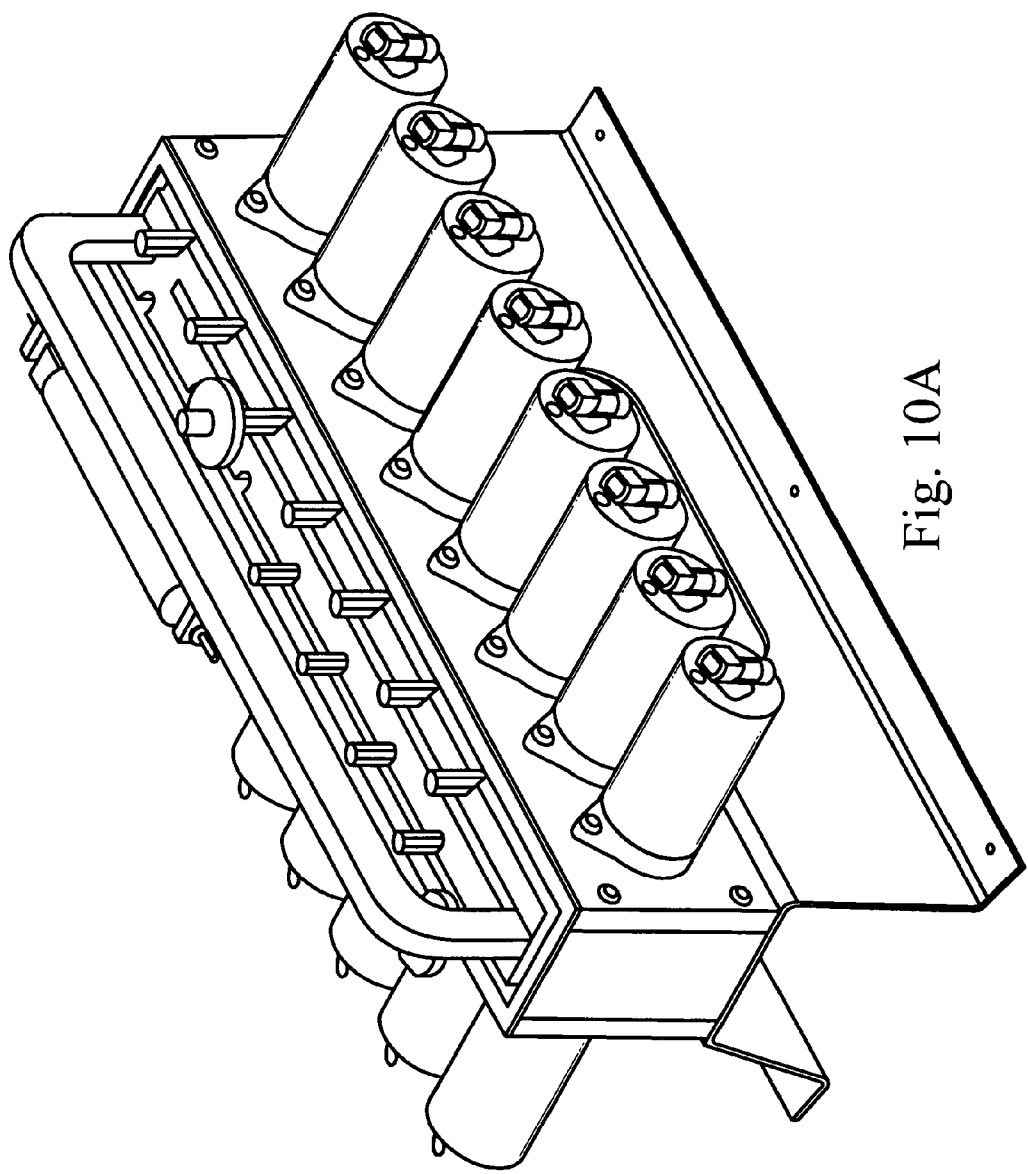
FIG. 10(A) provides a perspective view of a pinch valve manifold rack in accordance with one embodiment of the present invention; (B) provides a perspective view of the tubing rack of the pinch valve manifold rack in accordance with one embodiment of the present invention; (C) provides a cross sectional view of the tubing rack of the pinch valve manifold rack in accordance with one embodiment of the present invention; and (D) provides a side view of the pinch valve manifold rack in accordance with one embodiment of the present invention.
Figure 10B:
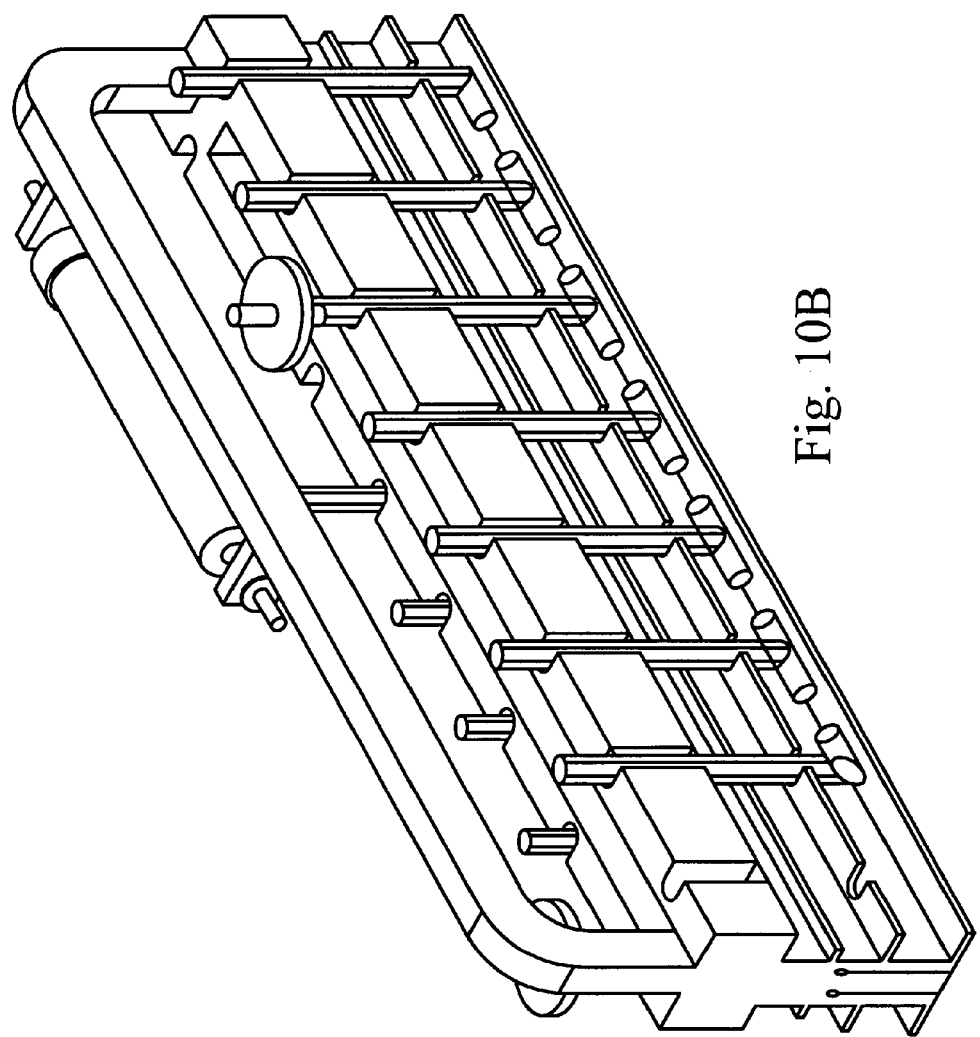
Figure 10C:
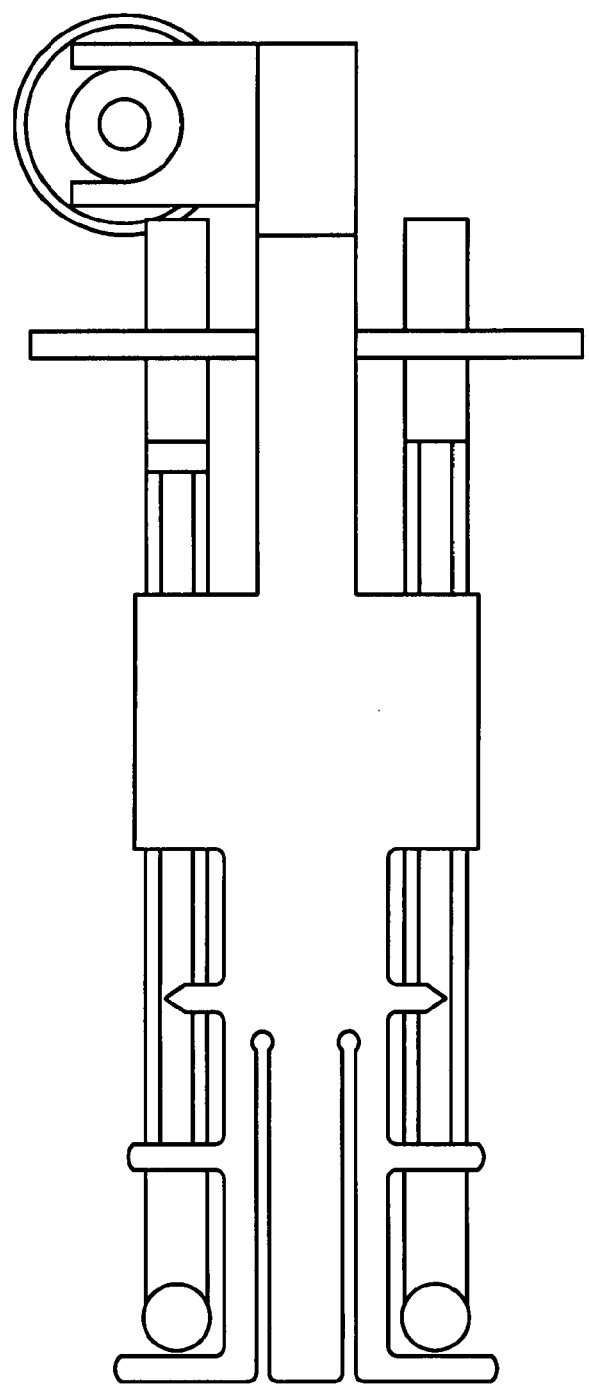
Figure 10D:
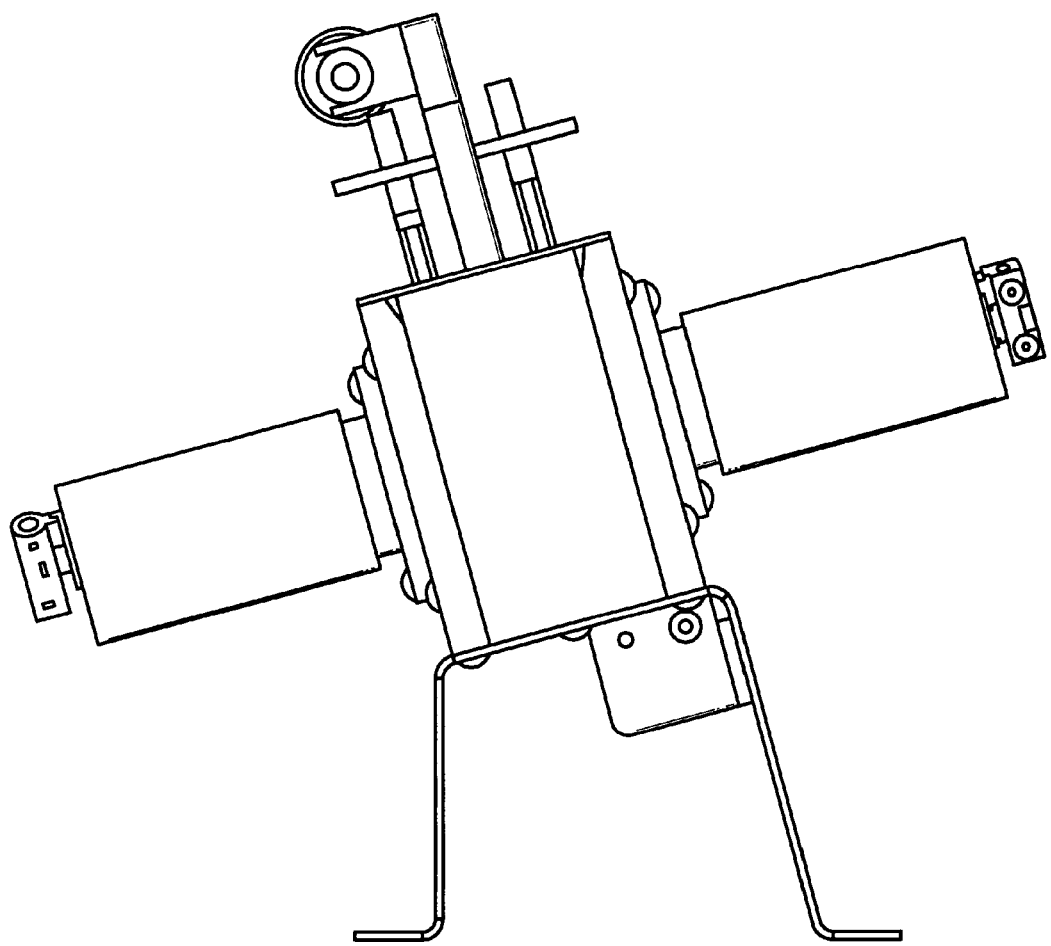

The Centrifuge Bowl of the cell processing apparatus is a lobed, two chamber construction consisting of an inner bowl and an outer bowl as shown in FIGS. 2A and 9B. The outer bowl is used primarily as an overflow chamber to store spent fat during the cell separation process. The novel design of the Centrifuge Bowl of the present invention provides optimized dual functionality. For instance, the inner chamber of the bowl is configured to provide a mixing zone, which is utilized in the digestion step of the cell processing methods disclosed herein, as well as a separation zone, (i.e., the lobes of the inner bowl) which optimizes the capture of a sufficiently purified cell pellet.

The lobes of the inner bowl of the present invention are specifically configured to optimize the collection of a endothelial cells and minimize collection of non-endothelial cell materials such as, for example red blood cells and other cell fragments. See FIGS. 2 and 9B. In an additional embodiment of the invention, as shown in FIG. 2(A)-(F), the Centrifuge Bowl comprises a twist lock coupling member which can be utilized to quickly and efficiently couple and uncouple the Centrifuge Bowl to the cell separation device.

Referring to FIG. 1 by way of non-limiting example, adipose tissue (Fat) is manually pushed from a syringe into the Centrifuge Bowl. The bowl is then manually loaded into the Cell Processing Device onto the drive mechanism which utilizes a twist lock coupling to secure it. A Centrifuge Chamber lid is then closed and hot air circulating within this chamber keeps it warm to 37° C.

A 60 ml syringe filled with chilled (about 2 C) collagenase solution is loaded into the syringe driver S1. A heating element integral to the syringe driver warms this solution to about 37° C. within approximately 15 minutes. After the collagenase solution has been heated to about 37° C., the Syringe Driver for S1 is activated and collagenase solution is pushed through valve V7 into the Centrifuge Bowl, while valve V8 remains closed to block flow through the 100 µm filter (F). The Centrifuge Bowl drive mechanism (motor) oscillates the bowl for an amount of time sufficient to allow for the collagenase to "digest" the adipose tissue. In a preferred embodiment, the amount of time sufficient to allow for the collagenase to digest the adipose tissue is approximately 30 minutes.

Fibrous tissue is then removed from the digested material. The Syringe Pump S1 draws back 50 ml of fluid via valve V8. The fibrous tissue is collected by the Filter (F) between these two valves. In one embodiment, the filter excludes material greater than 100 µm in size. The Syringe S1 pushes the first half of fluid temporarily to the waste tank (which is pristine for this step). A second pull is use to complete the evacuation of the centrifuge bowl and filter all material from it. The valves are then aligned to push the filtered material back into the bowl via valves V7. In one embodiment, the second half of the fluid comes straight from the syringe pump and the first half is drawn from the waste bag back into the S1 syringe and then pushed back into the Centrifuge Bowl.

The Centrifuge Bowl is then spun at about 3100 RPM for about 5 minutes. During centrifugation, the endothelial cells are separated from the digested material and deposited in the two lobes of the Centrifuge Bowl. The cells will tend to "pack" into the lobes and remain in the lobes until pushed out of them via separate means.

With the Centrifuge Bowl still spinning at about 3100 RPM additional M199E fluid is pushed from S2 into the bowl via valve V2. This fluid combined with the spinning motion displaces less dense fat cells to the center of the bowl. At least one notch aperture is located near the top center of the Centrifuge Bowl through which fat is directed from the inner bowl into an outer chamber via the centrifugal action of the inner bowl. This effectively removes much of the spent fat tissue from the inner bowl. See FIG. 2.

The Centrifuge Bowl is brought to rest and the collagenase/M199E mixture settles to the bottom of the inner bowl. This spent fluid is then sent to waste using syringe pump S1 via valves V7 and V9.

Fresh media M199E is added to the bowl via valve V2. A light spin is performed to "rinse" the bowl. This fluid is then sent to waste using syringe pump S1 via valves V8 and V9.

With the bowl empty and rinsed, the cell pellets still located in the centrifuge lobes are pushed back into the inner bowl via a rotating (or rotary) coupling and fluid moved through tubing. The rotating coupling in accordance with one embodiment of the invention is shown in FIG. 2. In a specific embodiment, the rotating coupling comprises at least one transport tube for use in adding and/or removing liquid from the inner chamber of the Centrifuge Bowl. In one embodiment, the rotating coupling comprises a transport tube for adding liquid to the inner chamber of the Centrifuge Bowl, and another transport tube for removing liquid from the inner chamber of the Centrifuge Bowl.

In accordance with another particular embodiment of the invention, cell pellets located in the centrifuge lobes are flushed from the lobes using a pressurized jet of fluid (jet spray) introduced from a nozzle member. In a particular embodiment, the nozzle member is in communication with a rotating coupling specifically adapted for use with the nozzle. FIG. 9 illustrates the jet spray nozzle and the rotating coupling in accordance with a specific embodiment of the invention. FIG. 9B further illustrates the rotating coupling and jet spray nozzle aligned in the centrifuge bowl.

By way of non-limiting example, the jet spray nozzle discharges fluid which impinges on a cell pellet "packed" or lodged into the centrifuge lobe. The cell pellet is broken up and/or dislodged from the lobe and fluid and cell pellet material are carried back to the bottom of the centrifuge bowl via gravity. In one embodiment, the jet spray nozzle is aligned with a support structure in the cell processing apparatus to fix its location (see e.g., FIG. 9B). In a preferred embodiment, the centrifuge motor is controlled by a computer and is adapted to indicate the position of the centrifuge bowl. Thus, the motor is capable of rotating the centrifuge bowl to align the jet spray nozzle with each lobe of the centrifuge bowl. For instance, after one lobe flush, the centrifuge bowl is rotated 180 degrees and the jet nozzle is activated to flush the second lobe. Accordingly, the jet spray nozzle is capable of efficiently dislodging the cell pellet in each lobe of the centrifuge bowl.

The fluid used for this purpose may be a fluid with a physiological concentration of sodium chloride at a physiological pH. In a preferred embodiment, the fluid used for this purpose is a 6:1 ratio of M199E and Serum, respectively. Serum is used to de-activate any residual collagenase in the cell product. Approximately 1 ml of cell material and 10 ml of M199E/Serum mixture is now in the bottom of the inner bowl.

In an embodiment of the present invention, the centrifuge lobes are adapted to include one or more selective filtering devices capable of using centrifugal force to concentrate or select out particular cell populations. In an embodiment, the selective filtering device(s) may be provided preferential alignment with the jet spray nozzle to recover the desired concentrate or cell population. In another embodiment, the cell separation apparatus is adapted to include one or more selective filters upstream of the collection module which are capable of selecting and capturing the desired cells, rerouting any excess media, and allowing the desired cells to be collected at a desired cells/ml concentration. In another embodiment, the cell separation apparatus of the present invention may include a cell counting and/or cell sorting device including, but not limited to, devices using known optical density or orifice electrical stimulation technology.

The cells to be processed by the cell separation apparatus of the present invention may include, for example, fibroblasts, smooth muscle cells, pericytes, macrophages, monocytes, plasma cells, mast cells, adipocytes, tissue-specific parenchymal cells, endothelial cells, urothelial cells, adipose derived stem cells and various other cell types encountered in tissue engineering applications and cell therapies, including undifferentiated adult stem cells from various tissue sources. Mitchell, J B. et al., Immunophenotype of Human Adipose-Derived Cells: Temporal Changes in Stromal-Associated and Stem Cell-Associated Markers, *Stem Cells* 2006, 24:376-385; McIntosh K. et al., The Immunogenicity of Human Adipose-Derived Cells: Temporal Changes In Vitro, *Stem Cells* 2006, 24:1246-1253; Kern S. et al., Comparative Analysis of Mesenchymal Stem Cells from Bone Marrow, Umbilical Cord Blood, or Adipose Tissue, *Stem Cells* 2006, 1294-1201. In a preferred embodiment, the cells are endothelial cells, more preferably human microvascular endothelial cells obtained from autologous microvascular rich adipose tissue as referred to in U.S. Pat. No. 4,820,626 (by Williams et al., issued Apr. 11, 1989), U.S. Pat. No. 5,230,693 (by Williams et al., issued Jul. 27, 1993), and U.S. Pat. No. 5,628,781 (by Williams et al., issued May 13, 1997), all of which are hereby incorporated by reference in their entireties. The adherent cells may be autologous, allogeneic, or xenogeneic, but preferably are autologous in origin.

Graft Sodding Module

Figure 6:
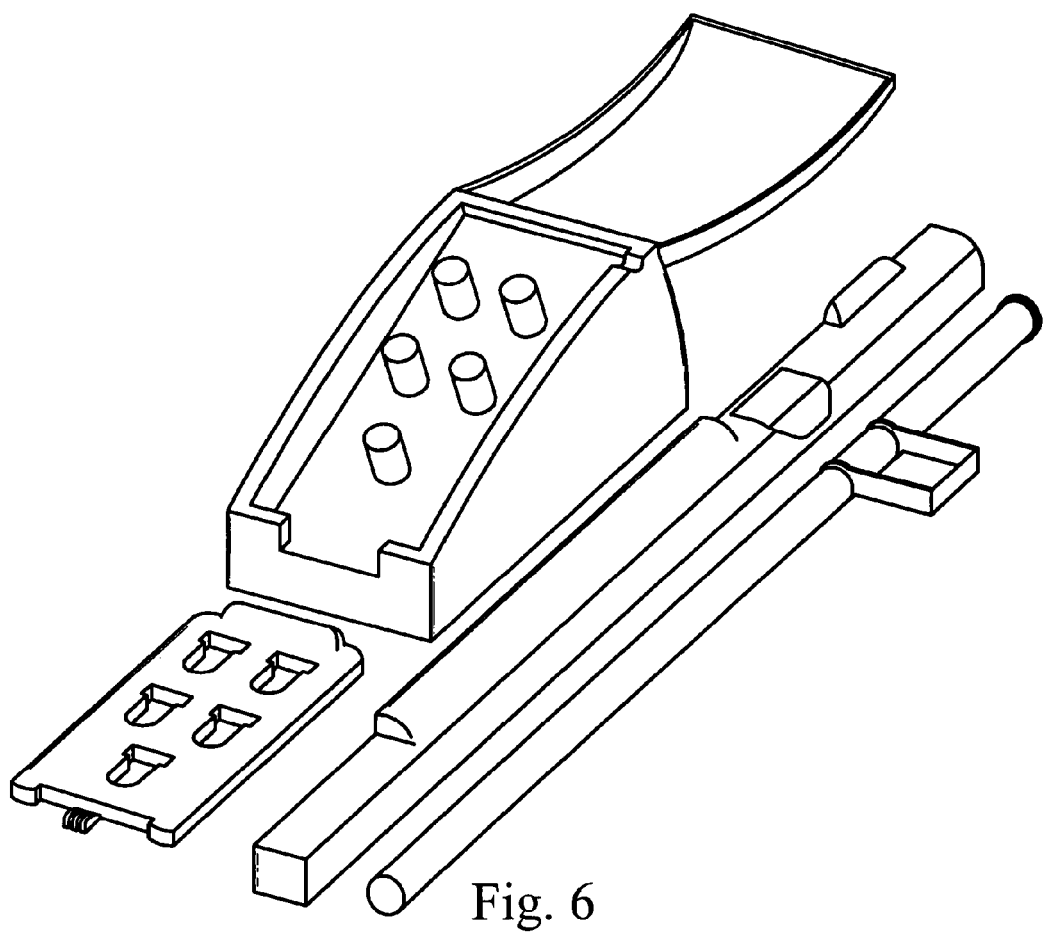
FIG. 6 depicts the graft sodding module in accordance with one embodiment of the present invention.

The cell separation apparatus of the present invention is designed to be modular such that components may be used and re-used with other devices and systems. In one embodiment, the cell separation apparatus is adapted for use with a cell sodding device or graft sodding module. The graft sodding module refers to the durable and disposable components that are necessary to apply the cells provided by the cell separation unit onto a porous graft scaffold using a pressure sodding technique. The graft sodding module durable and disposable components are shown in FIG. 6.

In an embodiment of the invention, the sodding module contains two durable components: the sodding unit durable and the graft chamber durable. These durable components physically mate with the cell separation durable to provide a power and communication connection. In another embodiment of the invention, the sodding module durables are controlled by the electronics in the cell separation module durable. The graft chamber durable provides secure mounting for the disposable graft and houses components necessary for heating of the chamber. The sodding durable contains the hardware (e.g., pinch valves, sensors) that is specifically required to manipulate flow through the graft chamber as needed for the pressure sodding application. In one embodiment, the sodding durable has a top flat surface with protruding durable equipment where the sodding disposable can be loaded. FIG. 6 shows the major components within the graft sodding durable and disposable components.

In a further embodiment, sodding disposable components include the disposable graft chamber and a sodding disposable tray. The scaffold or other substrate material is typically preloaded in the disposable graft chamber, which provides a sealed environment for delivery of liquids to the graft while prohibiting all other gaseous, liquid, and solid matter exchange with surroundings. In one embodiment, three ports on the graft chamber connect with tubing from the sodding disposable tray to provide inlet, transmural outlet, and lumenal outlet from the graft chamber. In an embodiment, the graft chamber rests inside the chamber durable which has a closing door to enclose the chamber during the sodding operation.

In an embodiment, the sodding disposable rigid tray includes all disposable components and connecting materials required for the sodding operation. The tray loads onto the flat surface of the sodding durable by aligning the pinch valves with the valve cutouts in the disposable tray and sliding forward to engage tubing in the pinch valves. The user connects the cell separation disposable, sodding disposable, and graft chamber disposable to form the complete flow path for sodding.

The separation and sodding media may be a commercially available media including DMEM, F12, AlphaMEM, University of Wisconsin Solution, etc., or any combination thereof, without or without additional factors, which may include heparin or other factors that accommodate the desired cell type.

Collection Module

Figure 7:
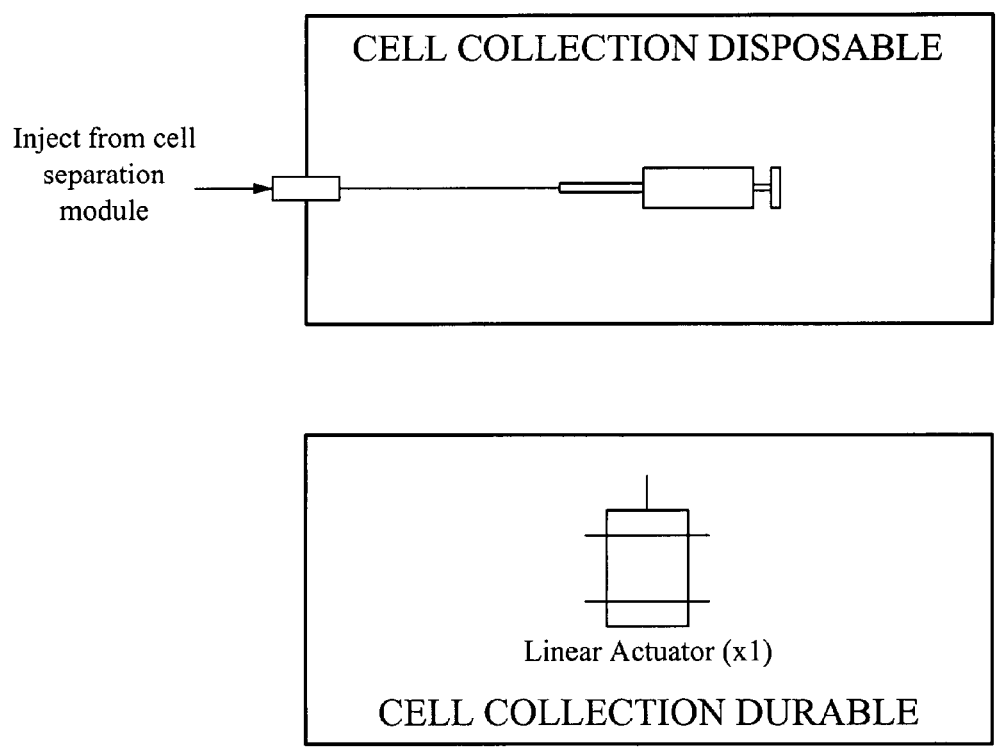
FIG. 7 depicts the cell collection module in accordance with one embodiment of the present invention.
Figure 8:
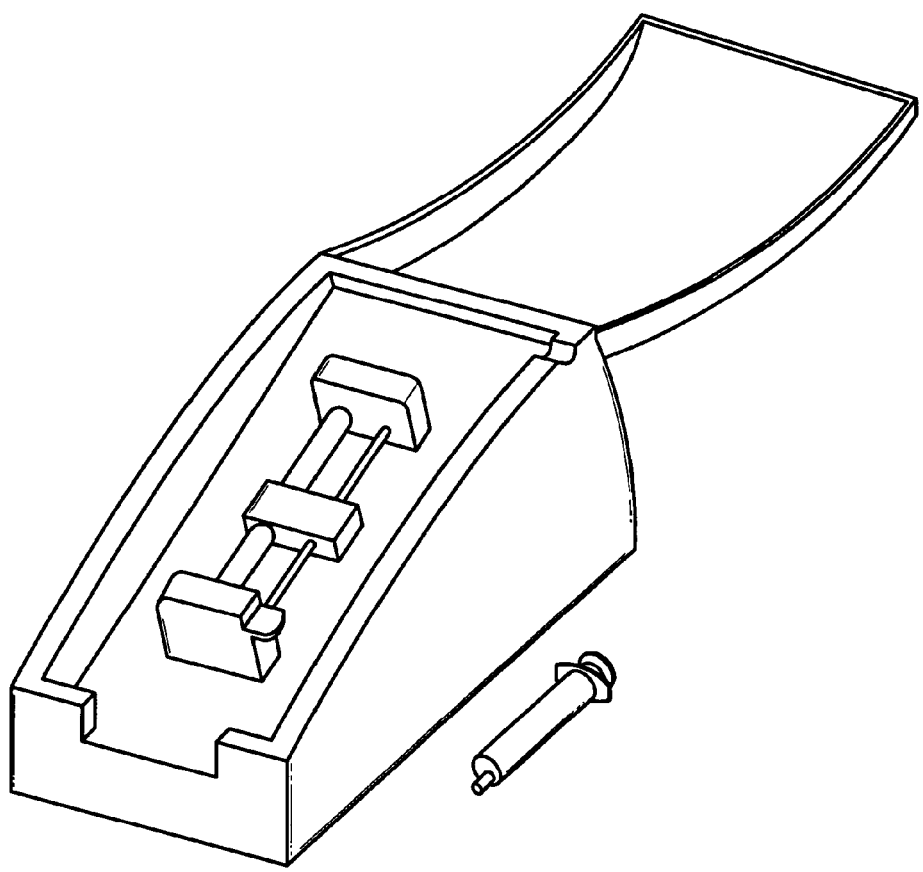
FIG. 8 is a perspective view of the cell collection module durables connected to the cell separation module with disposable components loaded for use in accordance with one embodiment of the present invention.

In an embodiment of the present invention, the cell separation apparatus is also designed to function with a collection module or collection device. The collection module or collection device refers to the durable and disposable components that are necessary to collect cells from the cell separation unit in a syringe for use in cell therapies. The cell collection module durable and disposable components are shown in FIG. 7. FIG. 8 shows the cell collection module durables connected to the cell separation module with disposable components loaded for use. In an embodiment, the collection module durable physically mates with the cell separation unit to provide a power and communication connection. The collection durable houses a linear actuator that interfaces with a syringe to automatically collect the cell product produced in the cell separation unit.

In another embodiment, the disposable component in the collection unit is the syringe to collect the cell product. The syringe is held in place by a clip on the collection unit durable. The top of the syringe is loaded into the durable such that the syringe plunger can be drawn by the motion of the actuator. The user connects the outlet tube from the cell separation module to the tip of the syringe.

The suspended cell product is removed via V8 into Syringe S0, and the cell product is then sent to a sterile container (not shown) attached to V5. In an embodiment of the invention, the sterile container is a syringe. In an additional embodiment, the second filter will typically be used between valve V5 and the container to remove and residual particles greater than about 30 microns.

Overview of Clinical (OR) Kit System

The clinical kit or operating room (OR) Kit of the present invention provides a sterile flow path, through which adipose tissue can be digested, separated, and pressure sodded onto a porous vascular graft scaffold. The system is also capable of pretreating the graft scaffold to prepare it for the pressure sodding operation. In one embodiment, the flow path comprises three disposable cartridges that interlock with a durable Clinical (OR) Kit system enclosure. The disposable cartridges include a flow path cartridge with fluid reservoirs, a disposable centrifuge cartridge comprising the cell separation apparatus of the present invention, and a disposable graft chamber that is pre-loaded with a graft scaffold. The Clinical (OR) Kit system is a self-contained, stand-alone system requiring only power to operate.

The system of the present invention is designed to require minimal operator interaction. The sterile graft chamber with preloaded graft scaffold, flow path cartridge, and centrifuge cartridge can be loaded into the Clinical (OR) Kit. The flow path cartridge can be preloaded with media which may be, for example, M199, M199E, PBS, Saline, and Di-Cation Free DPBS. In a preferred embodiment, the media is M199E.

The operator can then inject reconstituted collagenase from the hospital pharmacy, serum separated from the patient's blood and adipose tissue from the patient into the centrifuge and flow path cartridges through the appropriate injection ports. After completing this system set-up, the operator can start a sodding operation using an LCD interface on the Clinical (OR) Kit. With no additional interaction from the operator, the Clinical (OR) Kit will automatically perform all operations necessary to prepare a M199E/serum solution, pretreat the graft, digest adipose tissue using an externally prepared collagenase/PBS solution, centrifuge to isolate target cells, pressure sod the target cells into the porous graft scaffold, purge excess cells from the graft lumen, recirculate M199E/serum solution over the sodded graft, and isolate flow to the graft for harvest. FIG. 7 illustrates the inputs into the Clinical (OR) Kit durable enclosure for the graft processing operation.

Components of the envisioned Clinical (OR) Kit system include but are not necessarily limited to: an Clinical (OR) Kit enclosure, a front panel display (FPD), an Clinical (OR) Kit flow path cartridge, a graft chamber with preloaded scaffold, a main controller board (MCB), an analog board, a centrifuge, at least one pump, a fluid distribution system, various sensors and alarms, and a cell counter.

The Clinical (OR) Kit enclosure refers to the mechanical platform for the Clinical (OR) Kit which supplies power and gives mechanical stability to the Clinical (OR) Kit. The enclosure allows for entry cable connection for power. In a particular embodiment, this enclosure also houses all durable components for the instrument including motors, pinch valves, front panel display and sensors.

The Front Panel Display (FPD) provides a user-friendly graphical LCD display. The screens on the FPD display allow the operator to perform all the functions necessary to complete a pressure sodding operation in or adjacent to the OR. The operator will have the ability to begin a graft processing operation and view the status of the graft preparation at any time, but is restricted from changing parameters that may influence the quality of the sodded graft.

The flow path cartridge refers to the disposable, self-contained entity through which fluid flows throughout the system. FIG. 3 provides a conceptual illustration of the pathway through the flow path cartridge. The flow path cartridge includes a flow circuit, pump disposables, and fluid reservoirs for both feed and sump. The flow path cartridge mates with the cell processing or centrifuge cartridge and a graft chamber, which houses graft for pressure sodding in the operating room. The flow path cartridge physically mates with the enclosure. In an alternative embodiment, the disposable cell processing cartridge may be included as part of the flow path cartridge. In another embodiment, the pump disposable is separate from the flow path cartridge.

The graft chamber houses the graft scaffold for the graft processing operation. The scaffold is preloaded in the graft chamber, which provides a sealed environment for delivery of liquids to the graft while prohibiting all other gaseous, liquid, and solid matter exchange with surroundings. The graft substrate ("scaffold") materials used in the present invention may be any preferably permeable material of various sizes and geometries. The material may be natural or synthetic materials, including, but not limited to, polyethyleneterathalate, polyurethane, or expanded poly-tetrafluoroethylene (ePTFE). In another embodiment, the graft scaffold may be a biopolymer, such as collagen. The material may be preclotted and/or elastin, or allograft vessels, such as cryopreserved vein, decellularized vein or artery. In yet another embodiment, the scaffold may be a composite material such as an elastin scaffold with a polymeric coating, for example electrospun on the surface to improve mechanical properties. The material may be pre-clotted or pre-treated with a protein (e.g., albumin) or plasma, which in certain embodiments can serve to further enhance the adherence, spreading, and growth of tissue cells on the substrate material. The graft substrate or scaffolds may be constructed by any suitable method, including, but not limited to, those referred to in Liu, T. V. et al., 2004, Adv. Drug. Deliv. Rev. 56(11):1635-47; Nygren, P. A. et al., 2004, J. Immunol. Methods 290(1-2):3-28; Hutmacher, D. W. et al., 2004, Trends Biotechnol. 22(7):354-62; Webb, A. R. et al., 2004, Expert Opin. Biol. Ther. 4(6):801-12; and Yang, C. et al., 2004, BioDrugs 18(2):103-19.

The main controller board (MCB) in the Clinical (OR) Kit includes a microprocessor core module with appropriate interface to the analog board, which controls the peripheral sensors in the Clinical (OR) Kit assembly. Software resides on the main controller board processor which provides a straight forward user interface that ensures reliable and deterministic operation of the Clinical (OR) Kit. The analog board is peripheral to the MCB and is used to drive actuators and receive and condition sensor information.

A centrifuge separates the cells before pressure sodding into the graft. In one embodiment, the wetted centrifuge bowl is a separate disposable centrifuge cartridge, and the durable components are housed in the Clinical (OR) Kit enclosure.

One or more pumps drive flow through the system which are designed to keep pressure pulsations to a minimum. The wetted pump components are part of the flow path cartridge, and the pump shaft is driven by non-invasive means. In one embodiment of the present invention, the pumps are automatically self-priming during operation of the cell separation device.

The Clinical (OR) Kit system is designed to automatically advance through flow pathways necessary to pretreat a graft scaffold, prepare adipose tissue for sodding into the graft, apply the cells to the graft, and recirculate a M199E/serum solution over the graft to maintain viability until harvest. In one embodiment, tissue preparation includes treatment with collagenase that has been reconstituted from the powdered from outside of the Clinical (OR) Kit using a PBS solution, followed by centrifugation. The cells are then automatically resuspended in M199E/serum solution that is stored in a fluid reservoir within the Clinical (OR) Kit before the solution is applied to the graft. Fluid valves are configured to create these necessary pathways within the flow path cartridge and centrifuge cartridge and are controlled by Clinical (OR) Kit software. A constant pressure across the graft scaffold is maintained during the pressure sodding operation.

In a particular embodiment, the Clinical (OR) Kit includes sensors necessary to monitor and control temperature, pressure, and flowrate. Different flow path cartridges and graft chambers are loaded into the Clinical (OR) Kit to match the specific type of graft sodding to be completed (e.g. CABG, peripheral). The sensors are capable of detecting the presence of the flow path cartridge, centrifuge cartridge, and graft chamber to ensure the disposables are properly loaded. Additionally, the sensors are capable of detecting the type of flow path cartridge and graft chamber loaded to ensure the correct disposables are used.

The pressure sodding operation requires that 200,000 cells are applied to the graft scaffold for each cm2 of scaffold.

The Clinical (OR) Kit is capable of accepting input of collagenase reconstituted with PBS solution. In one embodiment, the kit accommodates at least about 60 mL of prepared collagenase solution. The kit accepts input of adipose tissue. In an embodiment, the adipose inlet accommodates between about 30-60 mL of adipose tissue. In another embodiment, the adipose inlet is positioned to allow the tissue to be introduced into an environment that is preheated to 37° C.

In an additional embodiment, the Clinical (OR) Kit system is capable of cutting adipose tissue using a consumable cutting adapter that can be optionally used depending on the tissue source. In a particular embodiment, the consumable cutting adapter is compatible for connection to the Tulip syringe. The system is additionally capable of heating the graft chamber, spaces where adipose tissue is loaded prior to digestion, and spaces for digestion to 37° C., and metering a volume of collagenase solution equal to the expected adipose tissue input.

The system is capable of mixing an adipose tissue and collagenase cell slurry. In a preferred embodiment, the system carries out the mixing and separation operations in a single centrifuge disposable, i.e. the cell processing device, that mates with the flow path cartridge and graft chamber. The system is also capable of removing fibrous material from the digested mixture. In an embodiment, the maximum allowable particle size in the resuspended cells does not exceed about 100 mm.

In an embodiment, the Clinical (OR) Kit system is capable of isolating a volume of "target cells" from an adipose tissue that has been digested by collagenase, and collecting the isolated target volume from separation. In a preferred embodiment, the system provides the following target pellet volume purity: less than 5% by volume of total isolated pellet volume for red blood cells; less than 1% by volume of total isolated pellet volume for adipose cells; less than 4% by volume of total isolated pellet volume for dead cells. In an additional preferred embodiment, all particles in the resuspension have a diameter less than or equal to 100 mm. In yet another preferred embodiment, the separation process does not expose the cells to a force greater than 900 G.

In an embodiment, the target cells are resuspended in a 6:1 volumetric mixture of M199E and serum. In another embodiment, the system provides means to control the number of cells applied to the graft scaffold, with a target number of around 200,000 cells/cm2 graft. Variation in this target number of +50% to −10% is acceptable. By way of example, the Clinical (OR) Kit system uses a volume of 6:1 M199E/serum solution that is proportional to the expected volume of adipose tissue loaded into the system.

In an embodiment, the system includes a disposable graft chamber that is preloaded with a graft scaffold for sodding. The graft chamber is capable of accommodating graft scaffolds with lengths from about 1-90 cm; graft inner diameters sizes from about 1-12 mm; and graft wall thickness from about 100-700 microns. The graft chamber provides a sealed environment for sodding which prohibits gaseous, liquid, and solid matter exchange with surroundings, except through graft chamber ports.

All individual disposable components of the system are adapted to mate with each other to form a continuous flow path. Further, all disposable wetted materials and coatings of the system of the present invention are biocompatible, and designed to withstand gamma irradiation to 25-40 kGy with at least 5% transmittance of clarity post-sterilization. Additionally, all non-disposable materials and coatings of the system, with the exception of internal electrical components, are compatible with typical disinfecting solutions including, for example, Cidex (glutaraldehyde antiseptic solution), 70% ethanol, 100% Isopropyl alcohol, and 10% bleach solution.

In one embodiment, the Clinical (OR) Kit system includes an electronics module with control electronics capable of driving, conditioning, acquiring and processing sensors for pressure, temperature, and flowrate. Pressure is measured at the graft chamber. In one embodiment, pressure across the scaffold wall is controlled at a target value of from about 1.5 psi, not to exceed 2.0 psi. In another embodiment, temperature is measured and maintained at about 37° C. in spaces for digestion and in the graft chamber. In another embodiment, flowrate measurement and/or control is implemented as needed to maintain the pressure requirement across the wall of the graft.

In one embodiment of the invention, software is resident in a central processor which controls electrical components and communication paths contained within the device enclosure. The system of the present invention is adapted such that the software prevents operation of any equipment if all disposable components are not correctly connected and interlocked in the enclosure.

Clinical (OR) Kit Operation

Figure 4:
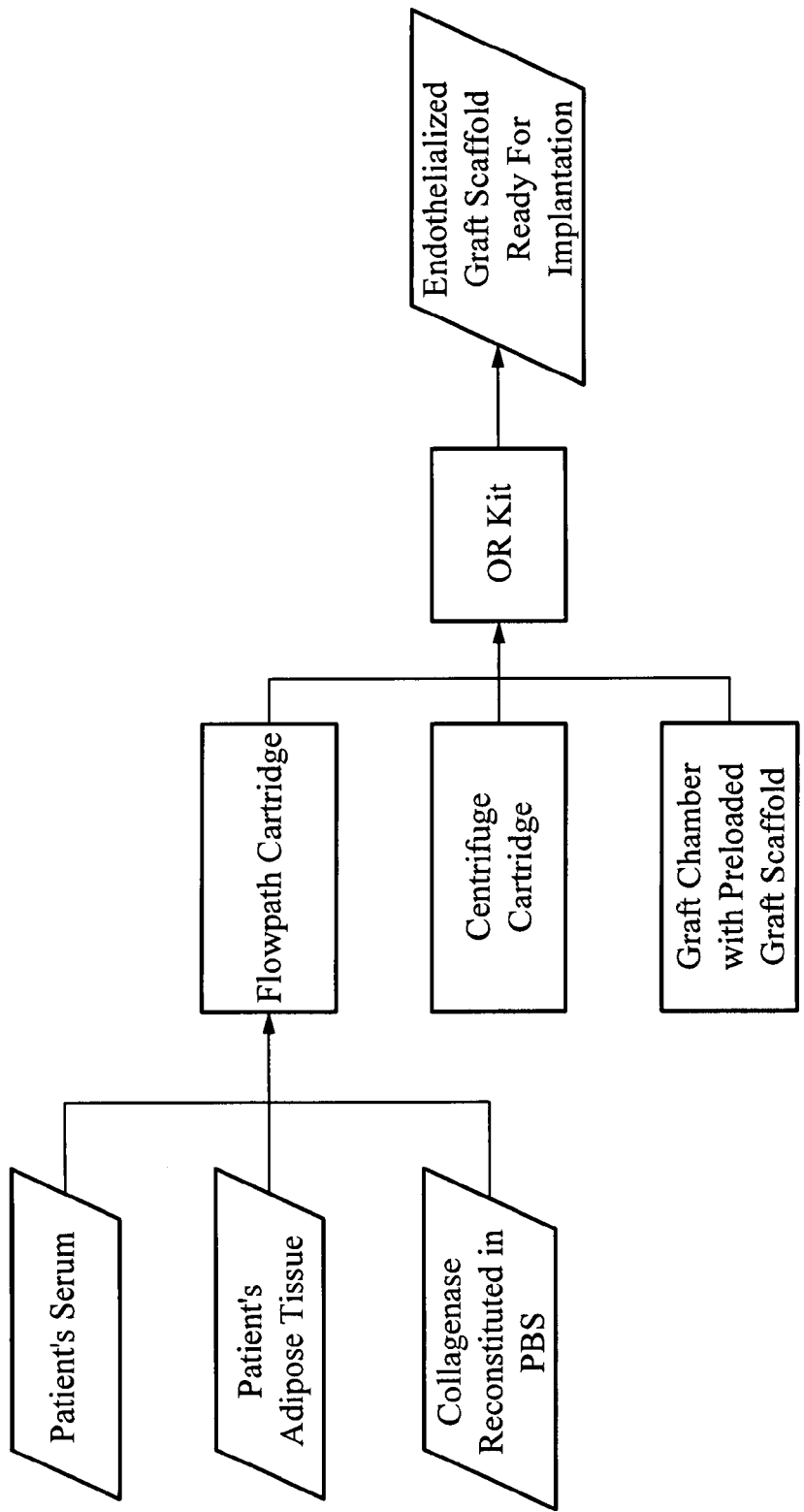
FIG. 4 is a schematic illustrating the Clinical (OR) Kit inputs in accordance with one embodiment of the present invention.

The Clinical (OR) Kit system automatically advances through flow pathways necessary to pretreat a graft scaffold, prepare adipose tissue for sodding into the graft, apply the cells to the graft, purge the graft lumen, and recirculate M199E/serum solution over the graft to maintain viability until harvest. FIG. 4 demonstrates the conceptual flow path between components within the Clinical (OR) Kit.

The illustrative systems described herein will typically include a microprocessor and associated software to control the system and automate one or more steps based on user input. The software may allow full or partial automation of, for example, controlling flow through tubular conduits by controlling pumps and valves, controlling temperature, and controlling cell separator and macerator devices. Preferably the system is fully automated, but capable of being reconfigured based on one or more input parameters. The systems may further include various sensors to detect or measure system parameters, such as pressures that would indicate a blockage, and signal same to the microprocessor or user. In one embodiment, the system is a hand-held system.

The controlled, sustained differential pressure gradient across the permeable scaffold material may be created by any suitable configuration, including, but not limited to, gear pumps, peristaltic pumps, diaphragm pumps, centrifugal pumps, and passive pressure heads created by a column of fluid, so long as the pressure is sufficiently sustained and at a magnitude sufficient to achieve the advantages of the invention. In a particularly preferred embodiment, the pressure is applied transmurally to a vascular graft scaffold using media containing endothelial cells at a pressure head of about 50 mmHg and for a duration of about 5 minutes.

Because at least a portion of the flow for the current invention is typically transmural, the flow rate is dependent upon the permeability of the graft material, and decreases as the cells are applied to the lumenal surface. Transmural flow rates before the introduction of cells can be from 5-50 ml/min depending on the graft material and generally decrease to 1-10 ml/min after the introduction of cells. Preferred endothelial cell numbers include 120,000-2,000,000 cells/cm$^2$ of luminal surface area, more preferably about 250,000 cells/cm$^2$.

Figure 5:
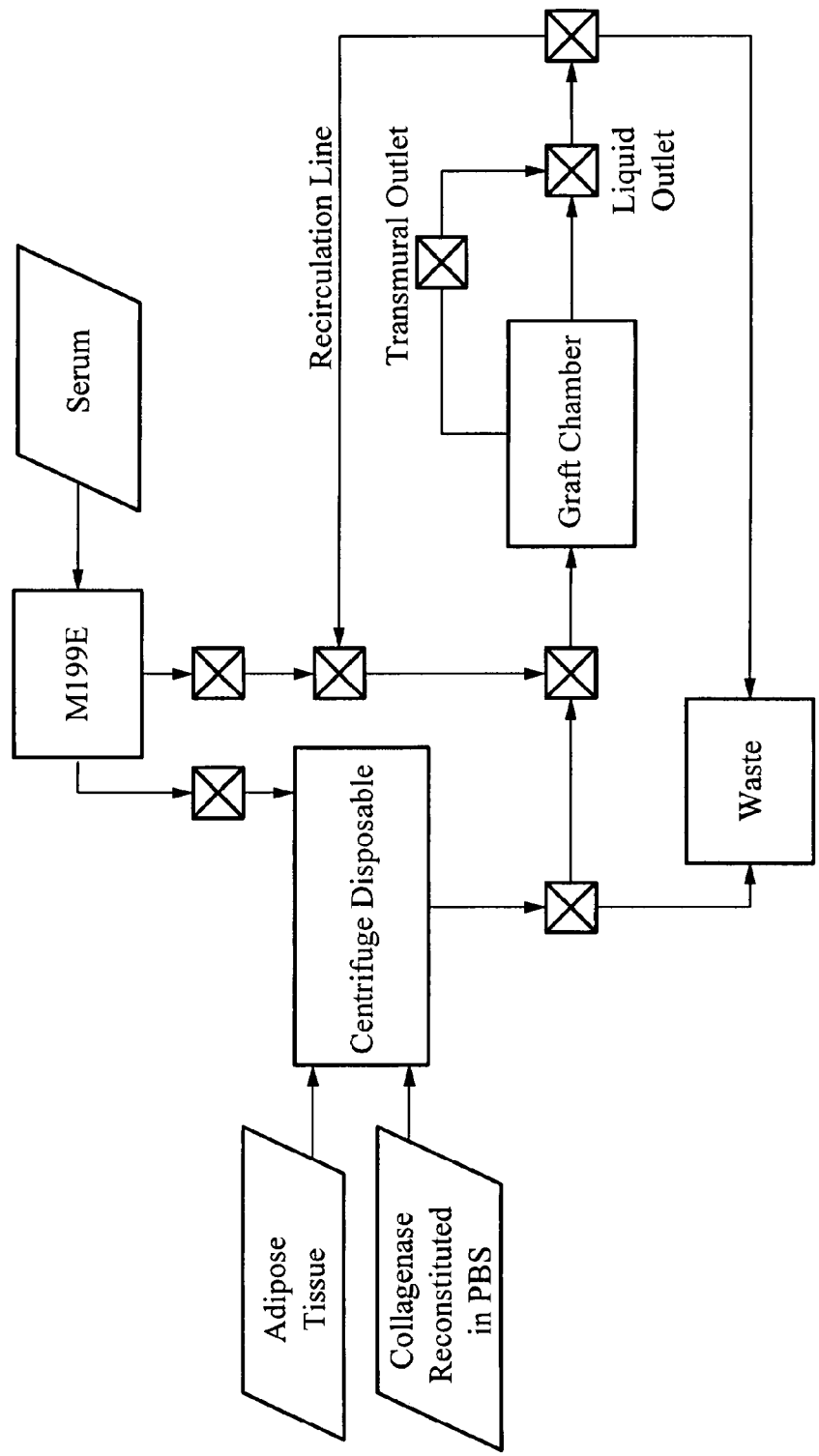
FIG. 5 is a schematic depicting the flow path of the Clinical (OR) Kit in accordance with one embodiment of the present invention.

In another particular embodiment of the present invention, the device system is modular, such that the tissue digestion and separation portion of the device can be used with interchangeable modules to either apply cells to a vascular graft or collect cells in a syringe. FIG. 5 shows the device assembled in a modular system. Because the cell separation portion of the device is housed in a distinct, separate unit, this embodiment also provides flexibility for pairing the cell separation unit other with other systems. Preferably, the device is divided into the three distinct modules: a cell separation module, a graft sodding module, and a cell collection module.

In one embodiment, the user installs the durable components required for the current application (i.e. graft sodding durables or cell collection durables) before switching on the device. When the device is switched on, it boots, detects that the durable modules are engaged properly, performs initial diagnostics, and goes into a standby mode. The user then presses a button near the display to initialize device set-up. The Clinical (OR) Kit enters a mode to allow installation of the disposables. The user is prompted to scan each disposable component using a bar code scanner mounted on the cell separation durable. When the user scans the disposable, the Clinical (OR) Kit will verify that the correct durables are in place, then guide the user through each step to load the disposable and make necessary tubing connections. The device will sense that the disposable components are properly loaded and ensure that all required disposables are installed for the current application. In a preferred embodiment, the barcode scanner is located on device such that scanning of the disposables does not interfere with loading of the disposables. The mounted barcode scanner is shown in FIG. 5.

After completing device set-up, the user interacts with the user interface to proceed. The device performs an air purge operation in which media and serum are pumped through the flow paths, pushing air to a waste collection point which has a vent port that allows air to escape to the atmosphere. The graft chamber is bypassed so that the graft is never exposed to air.

The user is then prompted to inject adipose into a port on the centrifuge disposable. The adipose tissue is macerated as it enters the centrifuge by passing through stationary blades. In a preferred embodiment, the protease solution is a collagenase/PBS solution. The user interface display indicates that the cell separation process is initiated.

In a preferred embodiment, from this point on, no user interaction is required until the entire Clinical (OR) Kit process is complete. The user interface display provides continuous updates on the process, indicating the specific operation being performed, the estimated time to complete the operation, and the estimated time to complete the entire process. In one embodiment, other important process parameters (temperatures, pump speed, etc.) can also be made available to the user via the display.

In an embodiment, the graft scaffold is packed in alcohol or other appropriate sterile substance within the disposable graft chamber. Graft preparation is concurrent with the cell separation steps provided below. The following steps are involved in preparing the graft for sodding. (1) Alcohol Purge—alcohol is purged from the graft chamber by flowing media through the graft chamber and directing the liquid outlet to waste; (2) Scaffold pretreatment—media is recirculated through the graft chamber until the cell suspension is available for graft sodding. The media can include, without limitation, M199, M199E, PBS, Saline, or Di-Cation Free DPBS. In a preferred embodiment, the media is a 6:1 mixture of M199E and serum from the patient.

The cell separation process is identical for sodding and cell collection operation modes. In one embodiment, the cell separation steps include: (1) adipose tissue digestion—the centrifuge is temperature controlled at about 37° C. and provides a low speed mixing action (mixing is maintained for an appropriate amount of time to ensure adequate digestion); (2) centrifugation—the centrifuge spins at high RPM, separating the adipose tissue into its constituent materials; and (3) endothelial cell isolation and resuspension. In one embodiment, the separated contents may be directed into a thin, transparent tube where an optical sensor detects the location and volume of the endothelial cells. Unwanted materials are directed to a waste reservoir, and a specific volume of endothelial cells is returned to the centrifuge. A 6:1 mixture of M199E and serum is pumped into the centrifuge. The centrifuge suspends the separated cells in the mixture by a low speed mixing action. The cell suspension is then pumped from the centrifuge through a 30-micron filter and directed to the graft sodding unit or the cell collection unit for collection into a syringe. FIG. 14 shows a cross-sectional view of one embodiment of the centrifuge bowl.

In the process of graft sodding, liquid passes between the separation module and graft module via the sodding module. Preferably, the graft is temperature controlled to about 37° C. In an embodiment, the graft sodding steps include cell sodding and "feed and bleed" flow. In the cell sodding step, the endothelial suspension is introduced into the recirculating flow path, allowing the cell suspension to flow into the graft at one end and out through the graft walls. Initially, the liquid mixture that leaves the graft chamber is directed to waste until the entire volume of cell suspension has entered the recirculating path. The cell suspension then recirculates until graft sodding is complete. The microporous ePTFE permits the passage of the media/serum mixture, but the cells are embedded into the ePTFE. During this process, transmural pressure is monitored by a pressure sensor in the sodding module. In the "feed and bleed" flow step, graft flow is switched to luminal when a specific transmural pressure is reached, indicating complete sodding. During this process, flow is alternately directed to waste and the pump(s) for recirculation. During periods when the flow is directed to waste, makeup media and serum are pumped from the reservoirs. The "feed and bleed" process is maintained for an appropriate amount of time.

In one embodiment of the cell collection process of the present invention, the cell suspension is pumped from the separation module to a syringe in the collection module. A linear actuator pulls the syringe plunger, drawing cell suspension into the syringe. FIG. 15 illustrates the system flow path.

Sustained pressure head, applied to a liquid medium with suspended cells across a permeable scaffold material, offers the advantage of rapid cell adhesion, without large pressure gradients as used in transient pressure sodding techniques. One skilled in the art could readily practice the invention with a myriad of cell types, scaffold materials and geometries with any number of device designs. Those skilled in the art will recognize, or be able to ascertain, many equivalents to the specific embodiments of the invention described herein using no more than routine experimentation. Such equivalents are intended to be encompassed by the claims.

The present invention provides devices and methods of preparing various tissue implants or grafts by applying pressure, preferably sustained low magnitude pressure, for adhering or "sodding" cells onto any suitable graft scaffolds or other permeable substrate materials. In a specific embodiment, the tissue is a tubular tissue, such as a vascular tissue. However, the invention is also applicable to any type of tissue grafts involving the adhesion of cells to scaffolds or other substrate materials, including, but not limited to, skin, cartilage, bone, bone marrow, tendon, ligament, gastrointestinal tract, genitourinary tracts, liver, pancreas, kidney, adrenal gland, mucosal epithelium, and nerve grafts. The method is particularly well suited to tubular tissues, including, but not limited to, those of the cardiovascular system and the urinary system.

The term "sustained low magnitude pressure" as used herein means pressure having a head of about 10 mmHg, about 15 mmHg, about 20 mmHg, about 25 mmHg and about 30 mmHg and about 55 mmHg, for about 5 min, about 20 min, about 30 min, about 40 min, about 50 min, about 1 hour, about 1.5 hours, about 2 hours, about 2.5 hours, about 3 hours, about 4 hours, about 5 hours or about 6 hours, to enhance the adhesion, growth and/or differentiation of the cells. One of ordinary skill in the art can select appropriate conditions for applying specific low magnitude sustained pressures according to the types of cells, tissue grafts, substrate materials, and given the teachings herein.

The term "transmural pressure or flow" as used herein refers to pressure or flow from one side to the other side of a graft scaffold, across the wall of the graft scaffold. Where the graft scaffold is a tubular graft scaffold, the term refers to pressure or flow from the lumen or intracapillary (IC) space of the graft to the outside or extracapillary (EC) space of the graft.

The term "translumenal pressure or flow" as used herein refers to pressure or flow through the lumen of a tubular graft. The terms "translumenal flow" and "translumenal perfusion" may be used interchangeably. While translumenal perfusion is not required for cellular adhesion in the present invention, it may be used, for example, after the transmural flow to provide a training or cleansing effect. In this case, flow rates up to and including physiologic flow rates (~160 ml/min) are preferred, although flow rates as low as 5 ml/min typically are sufficient to provide cellular adhesion capable of withstanding subsequent physiologic flow.

Therapeutic Uses

The tissue grafts and cell suspensions prepared by the above-described devices can be employed in a myriad of therapeutic uses. For example, in one embodiment of the invention methods are provided for revascularizing a tissue or organ of a subject in need thereof, by implanting into the tissue or organ at least one tissue graft or cell suspension that is prepared by any of the above-described devices. The terms "revascularize", "revascularizing", "neovascularization", or "revascularization" as used herein refer to revising an existing vascular network or establishing a new functional or substantially functional vascular network in a tissue or organ that has an avascular or hypovascular zone, typically due to disease, congenital defect, or injury.

In an embodiment, the tissue graft or cell suspension comprises cells selected from the group consisting of skin, skeletal muscle, cardiac muscle, atrial appendage of the heart, lung, mesentery, or adipose tissue. The adipose tissue may be from omental fat, properitoneal fat, perirenal fat, pericardial fat, subcutaneous fat, breast fat, or epididymal fat.

In certain embodiments, the tissue graft or cell suspension further comprises appropriate stromal cells, stem cells, Relevant Cells, or combinations thereof. As used herein, the term "stem cells" is used in a broad sense and includes traditional stem cells, adipose derived stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including method for isolating and culturing them, may be found in, among other places, Embryonic Stem Cells, Methods and Protocols, Turksen, ed., Humana Press, 2002; Weisman et al., Annu Rev. Cell. Dev. Biol. 17:387 403; Pittinger et al., Science, 284:143 47, 1999; Animal Cell Culture, Masters, ed., Oxford University Press, 2000; Jackson et al., PNAS 96 (Shepherd B R et al. Rapid perfusion and network remodeling in a microvascular construct after implantation. *Arterioscler Thromb Vasc Biol* 24: 898-904, 2004):14482 86, 1999; Zuk et al., Tissue Engineering, 7:211 228, 2001 ("Zuk et al."); Atala and Lanza, eds., Academic Press, 2001 (Atala, et al.), particularly Chapters 33 41; and U.S. Pat. Nos. 5,559,022, 5,672,346 and 5,827,735. Descriptions of stromal cells, including methods for isolating them, may be found in, among other places, Prockop, Science, 276:71 74, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963,489. The skilled artisan will understand that the stem cells and/or stromal cells selected for inclusion in a tissue graft or cell suspension are typically appropriate for the intended use of that construct. In certain embodiments, the tissue graft or cell suspension once implanted in vivo, will develop a functional vascular bed and inosculate with the surrounding functional vascular system and perfuse, or be capable of perfusing, the damaged tissue or organ.

According to certain methods for revascularizing tissues or organs, at least one tissue graft or cell suspension is combined with said tissue or organ and a revascularized tissue or organ is generated. According to certain methods for revascularizing tissues or organs, the term "combining" comprises placing or implanting at least one tissue graft or cell suspension on any surface of, within, between the layers of, or adjacent to, said tissue or organ. In certain embodiment, the tissue graft or cell suspension is implanted in the tissue or organ by injection. In certain embodiments, such injected construct will polymerize in situ, following implantation. In certain embodiments, such injected tissue graft or cell suspension comprises at least one cultured microvessel construct, at least one freshly isolated microvessel construct, or both. In certain embodiments, combining comprises attaching at least one tissue graft or cell suspension to at least one tissue or organ in need of revascularizing, using techniques known in the art, such as described above.

The skilled artisan understands that certain tissues and organs are covered by or contain a layer of fibrous tissue, connective tissue, fatty tissue, or the like, and that the underlying tissue or organ can be revascularized without removing this layer. Such a layer may be naturally occurring (such as a serosal layer, mucous membrane, fibrous capsule, or the like), may result form fibrosis, necrosis, or ischemia, due to disease, defect, injury, or biochemical deficiency. Typically, the microvessel fragments of the tissue graft or cell suspension can penetrate such a layer and inosculate with the vasculature of the underlying tissue or organ, revascularizing the tissue or organ. Thus, combining the tissue graft or cell suspension with the tissue or organ in need of revascularization, comprises placing the tissue graft or cell suspension on or in such layer. For example, but not limited to, placing the tissue graft or cell suspension on the meninges to revascularize brain tissue; the epicardium to revascularize the myocardium; the peritoneum and/or serosa, to revascularize portions of the large intestine; the conjunctiva and/or subconjunctiva to revascularize the eye; the tracheal surface to revascularize the trachea; the bucchal mucosa to revascularize the mouth; the pleural and/or serosal surface to revascularize the lung; the pleural and/or peritoneal surface to revascularize the diaphragm; the skin to revascularize non-healing skin ulcers, such as diabetic ulcers; the pericardial surface to revascularize the pericardium; and the like.

In certain embodiments, the tissue graft or cell suspension, when combined with the tissue or organ within the animal or human, will develop functional vascular bed and inosculate with the surrounding functional vascular system and perfuse the damaged tissue or organ. In certain embodiments, the implanted tissue graft or cell suspension serves as a nucleation site for revascularizing the damaged tissue or organ. In certain embodiments, appropriate stem cells, stromal cells, and/or Relevant Cells from the tissue graft or cell suspension will support the restructuring and repair of the damaged tissue or organ. Constructs comprising genetically engineered cells may produce recombinant products that are distributed systemically via the bloodstream or delivered to the local microenvironment to induce repair, wound healing, or the like.

In a particular embodiment, the tissue graft or cell suspension comprises endothelial cells which are capable of differentiating into, without limitation, a neuron, myocardiocyte, chondrocyte, pancreatic anincar cell, pancreatic endocrine cells including islet of Langerhans, hepatocyte, renal epithelial cell, parathyroid cell, Leydig cell, sertoli cell, gonocyte, oocyte, blastocyst, Kupffer cell, lymphocyte, fibroblast, myocyte, myoblast, satellite cell, adipocyte, preadipocyte, osteocyte, osteoblast, osteoclast, chondrocyte, biliary epithelial cell, Purkinje cell, and pacemaker cell.

In another particular embodiment, the tissue graft or cell suspension comprises at least one stem cell, progenitor cell or Relevant Cell, which may be without limitation a neuron, myocardiocyte, chondrocyte, pancreatic anincar cell, pancreatic endocrine cells including islet of Langerhans, hepatocyte, renal epithelial cell, parathyroid cell, Leydig cell, sertoli cell, gonocyte, oocyte, blastocyst, Kupffer cell, lymphocyte, fibroblast, myocyte, myoblast, satellite cell, adipocyte, preadipocyte, osteocyte, osteoblast, osteoclast, chondrocyte, biliary epithelial cell, Purkinje cell, and pacemaker cell.

The term "Relevant Cell(s)" as used herein refers to cells that are appropriate for incorporation into a tissue graft or cell suspension prepared by the devices of the present invention, based on the intended use of that tissue graft or cell suspension. By way of example, Relevant Cells that are appropriate for the repair, restructuring, or repopulation of damaged liver may include, without limitation, hepatocytes, biliary epithelial cells, Kupffer cells, fibroblasts, and the like. Exemplary Relevant Cells for incorporation into tissue graft or cell suspensions include neurons, myocardiocytes, myocytes, chondrocytes, pancreatic acinar cells, islets of Langerhans, osteocytes, hepatocytes, Kupffer cells, fibroblasts, myocytes, myoblasts, satellite cells, endothelial cells, adipocytes, preadipocytes, biliary epithelial cells, and the like. These types of cells may be isolated and cultured by conventional techniques known in the art. Exemplary techniques can be found in, among other places, Atala et al., particularly Chapters 9-32; Freshney, Culture of Animal Cells A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022.

The skilled artisan will appreciate that such stromal cells, stem cells, and/or Relevant Cells may be incorporated into the tissue graft or cell suspension during or after preparation. For example, but not limited to, combining the cell suspension, stem cells, Relevant Cells, and/or stromal cells in a liquid three-dimensional culture, such as collagen, fibrin, or the like, or seeding or sodding stem cells, Relevant Cells, and/or stromal cells in or on the tissue graft may be achieved. Exemplary combinations of appropriate stem cells, stromal cells, and Relevant Cells for incorporation into tissue grafts or cell suspensions include: islets of Langerhans and/or pancreatic acinar cells in a tissue graft or cell suspension for revascularizing a damaged pancreas; hepatocytes, hepatic progenitor cells, Kupffer cells, endothelial cells, endodermal stem cells, liver fibroblasts, and/or liver reserve cells in a tissue graft or cell suspension for revascularizing a damaged liver. For example, but not limited to, appropriate stem cells or stromal cells for a tissue graft or cell suspension for vascularizing, repairing, and reconstructing a damaged or disease liver might comprise liver reserve cells, liver progenitor cells, such as, but not limited to, liver fibroblasts, embryonic stem cells, liver stem cells, cardiomyocytes, Purkinje cells, pacemaker cells, myoblasts, mesenchymal stem cells, satellite cells, and/or bone marrow stem cells for revascularizing a damaged or ischemic heart (see, e.g., Atkins et al., J. of Heart and Lung Transplantation, December 1999, at pages 1173 80; Tomita et al., Cardiovascular Research Institute, American Heart Association, 1999, at pages 92 101; Sakai et al., Cardiovascular Research Institute, American Heart Association, 1999, at pages 108 14), and the like.

In one embodiment, the tissue graft or cell suspension further comprises an agent selected from the group consisting of cytokines, chemokines, antibiotics, drugs, analgesic agents, anti-inflammatory agents, immunosuppressive agents, or combinations thereof. Exemplary cytokines may include, without limitation, angiogenin, vascular endothelial growth factor (VEGF, including, but not limited to VEGF-165), interleukins, fibroblast growth factors, for example, but not limited to, FGF-1 and FGF-2, hepatocyte growth factor, (HGF), transforming growth factor beta (TGF-.beta.), endothelins (such as ET-1, ET-2, and ET-3), insulin-like growth factor (IGF-1), angiopoietins (such as Ang-1, Ang-2, Ang-3/4), angiopoietin-like proteins (such as ANGPTL1, ANGPTL-2, ANGPTL-3, and ANGPTL-4), platelet-derived growth factor (PDGF), including, but not limited to, PDGF-AA, PDGF-BB and PDGF-AB, epidermal growth factor (EGF), endothelial cell growth factor (ECGF), including ECGS, platelet-derived endothelial cell growth factor (PD-ECGF), placenta growth factor (PLGF), and the like. Cytokines, including recombinant cytokines, and chemokines are typically commercially available from numerous sources, for example, R & D Systems (Minneapolis, Minn.); Endogen (Woburn, Wash.); and Sigma (St. Louis, Mo.). The skilled artisan will understand that the choice of chemokines and cytokines for incorporation into particular tissue graft or cell suspensions will depend, in part, on the target tissue or organ to be vascularized, revascularized, augmented or reconstructed.

In certain embodiments, tissue graft or cell suspensions further comprise at least one genetically engineered cell. In certain embodiments, tissue graft or cell suspensions comprising at least one genetically engineered cell will constitutively express or inducibly express at least one gene product encoded by at least one genetically engineered cell due to the genetic alterations within at least one genetically engineered cell induced by techniques known in the art. Descriptions of exemplary genetic engineering techniques can be found in, among other places, Ausubel et al., Current Protocols in Molecular Biology (including supplements through March 2002), John Wiley & Sons, New York, N.Y., 1989; Sambrook et al., Molecular Cloning: A Laboratory Manual, 2.sup.nd Ed., Cold Spring Harbor Laboratory Press, Cold Spring Harbor, N.Y., 1989; Sambrook and Russell, Molecular Cloning: A Laboratory Manual, 3.sup.rd Ed., Cold Spring Harbor Laboratory Press, Cold Spring Harbor, N.Y., 2001; Beaucage et al., Current Protocols in Nucleic Acid Chemistry, John Wiley & Sons, New York, N.Y., 2000 (including supplements through March 2002); Short Protocols in Molecular Biology, 4.sup.th Ed., Ausbel, Brent, and Moore, eds., John Wiley & Sons, New York, N.Y., 1999; Davis et al., Basic Methods in Molecular Biology, McGraw Hill Professional Publishing, 1995; Molecular Biology Protocols (see the highveld.com website), and Protocol Online (protocol-online.net). Exemplary gene products for genetically modifying the genetically engineered cells of the invention include plasminogen activator, soluble CD4, Factor VIII, Factor IX, von Willebrand Factor, urokinase, hirudin, interferons, including alpha-, beta- and gamma-interferon, tumor necrosis factor, interleukins, hematopoietic growth factor, antibodies, glucocerebrosidase, adenosine deaminase, phenylalanine hydroxylase, human growth hormone, insulin, erythropoietin, VEGF, angiopoietin, hepatocyte growth factor, PLGF, and the like.

In an embodiment of the invention, the tissue or organ is selected from the group consisting of heart tissue, lung tissue, cardiac muscle tissue, striated muscle tissue, liver tissue, pancreatic tissue, cartilage, bone, pericardium, peritoneum, kidney, smooth muscle, skin, mucosal tissue, small intestine, and large intestine and adipose tissue.

The step of injecting a cell suspension into a subject tissue or organ may include, without limitation, using at least one syringe, needle, cannula, catheter, tube, or microneedle. The terms "injecting", "injection", or variations thereof as used herein shall refer to any means of ejecting or extruding a substance, typically through a tube or structure comprising a bore or external opening. Such tube or structure can be flexible, inflexible, or can comprise at least one flexible portion and at least one inflexible portion. Exemplary injection means include a syringe with or without a needle, a cannula, a catheter, flexible tubing, and the like. Delivery of the particular cell suspension might also be accomplished through the use of devices that permeablize tissue, such as microneedles. In contrast to traditional injections with standard-gauge hypodermic needles, microneedle (typically defined by a radius of curvature .about.1 um) or microneedle arrays permeabilize the skin or endothelial cell layer by producing microscopic holes. These holes, in effect, act as conduits for materials delivery and may enhance the attachment or delivery of a cell suspension of the present invention to a vessel, tissue, or organ. Thus, the skilled artisan will understand that any structure comprising a bore or external opening through which at least one cell suspension can be extruded on or into a tissue or organ, or any structure that can permeabilize the surface of a tissue or and organ, including an engineered tissue, is within the intended scope of the invention. In certain embodiments, such injected construct polymerizes in vitro, following injection.

In a particular embodiment, the tissue graft or cell suspension of the present invention comprises cells selected from the group consisting of skin, skeletal muscle, cardiac muscle, atrial appendage of the heart, lung, mesentery, or adipose tissue. The adipose tissue may be selected from the group consisting of omental fat, properitoneal fat, perirenal fat, pericardial fat, subcutaneous fat, breast fat, or epididymal fat.

Also provided are methods for augmenting a tissue or organ of a subject in need thereof, comprising implanting into the organ or tissue a tissue graft prepared by the devices of the present invention or injecting into the tissue or organ a cell suspension prepared by the devices of the present invention. As used herein, "augmenting" refers to increasing the volume and/or density of the tissue or organ.

Methods are also provided for regenerating a tissue or organ in a subject by implanting into the tissue or organ at least one tissue graft prepared by the devices described herein or by injecting into the tissue or organ at least one cell suspension prepared by the devices of the invention. As used herein, "regenerating" refers to replacing lost, diseased or otherwise damaged tissue by the formation of new tissue.

A skilled artisan will appreciate that the subject of the present invention may be any animal, including amphibians, birds, fish, mammals, and marsupials, but is preferably a mammal (e.g., a human; a domestic animal, such as a cat, dog, monkey, mouse, and rat; or a commercial animal, such as a cow, horse or pig). Additionally, the subject of the present invention may be of any age, including a fetus, an embryo, a child, and an adult. In a preferred embodiment of the present invention, the subject is human. In one embodiment, the subject is a horse and methods of the subject invention are used to regenerate tissues in and around the hooves of the animal. In further embodiments, the subject is a human, and the methods of tissue regeneration are used to prevent or treat, for example arthritis and diseases of the eye, including but not limited to, glaucoma and macular degeneration.

Additionally, methods for reconstructing a tissue or organ in a subject in need thereof comprising implanting into the tissue or organ at least one tissue graft prepared by the devices described herein or by injecting into the tissue or organ at least one cell suspension prepared by these devices. As used herein, "reconstructing" refers to rebuilding, reconstituting, reshaping and/or restoring a tissue or organ. In one embodiment of the invention, for example the subject has cellulite, and the subject is administered a subcutaneous injection of an appropriate cell suspension in order to locally reconstruct the adipose tissue, thus improving the cosmetic appearance of the subject. In one embodiment, the subject is a post-surgical subject.

Also provided are methods for treating or preventing primary and secondary infections in a tissue or organ of a subject by implanting into the tissue or organ at least one tissue graft prepared by the devices described herein or by injecting into the tissue or organ at least one cell suspension prepared by these devices.

Methods for using the cell suspensions and tissue grafts prepared by the devices of the present invention to prevent the formation of scar tissue in a tissue or organ, and/or to treat or prevent inflammation in a tissue or organ of a subject are also provided.

Also provided are methods for preventing adhesion formation in a tissue or organ of a subject in need thereof by injecting into the tissue or organ at least one cell suspension or tissue graft prepared by the devices of the invention.

In one embodiment, a method is provided for treating or preventing acute myocardial infarction in a subject by injecting into the heart at least one cell suspension prepared by any of the devices described herein, wherein vasculature to the heart tissue is increased. In another embodiment, methods for treating myocarditis in a subject are provided comprising injecting into the pericardial fluid of the subject at least one cell suspension prepared by any of the devices of present invention.

Methods for treating a wound in a subject by injecting the wound with at least one cell suspension prepared by the device of the present invention are also provided. In one embodiment, the subject is a post-surgical subject.

The current invention provides sustained pressure sodding and automation of the clinical procedures of separating a desired fraction of the patient's cells from tissue and filtering, rinsing, heating, macerating, proteolytically releasing, separating, resuspending, and pressure sodding the cells onto a permeable graft. Those skilled in the art will recognize, or be able to ascertain, many equivalents to the embodiments of the inventions described herein using no more than routine experimentation. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

The above description and example are only illustrative of preferred embodiments which achieve the objects, features, and advantages of the present invention, and it is not intended that the present invention be limited thereto.

What is claimed is:

1. A method for separating cells comprising:
    a) adding an amount of tissue comprising fat cells to an inner bow of a cell separation apparatus, the cell separation apparatus comprising:
      (i) a medium reservoir;
      (ii) a cell processing device comprising (A) at least one inlet and (B) at least one outlet, (C) a first lobe and (D) a second lobe;
      (iii) at least one pump; and
      (iv) at least one valve adapted to divert or prevent fluid flow, wherein the at least one pump and at least one valve are in fluid communication with one another; and wherein the inner bowl is in fluid communication with an outer bowl;
    b) heating the tissue to a temperature of about 37°C;
    c) adding an effective amount of collagenase to the inner bowl;
    d) digesting the tissue by oscillating the inner bowl for an effective amount of time;
    e) removing fibrous tissue from the digested tissue;
    f) spinning the inner bowl at about 3100 RPM for about 5 minutes;
    g) displacing the fat cells to the center of the inner bowl by adding fluid to the inner bowl;
    h) directing the fat cells through at least one aperture in the inner bowl into the outer bowl by centrifugal action;
    i) rinsing the inner bowl with fluid;
    j) directing at least one cell pellet from at least one lobe of the inner bowl to the bottom or the inner bowl;
    k) optionally, adding fluid to the inner bowl and spinning the inner bowl at about 3100 RPM for about 5 minutes; and
    l) collecting the at least one cell pellet.

2. The method of claim 1, wherein the tissue is selected from the group consisting of adipose tissue, bone marrow, skin, and skeletal muscle.

3. The method of claim 1, wherein the tissue is adipose tissue.

4. The method of claim 1, wherein the fluid is a solution containing a physiological concentration of sodium chloride at a physiological pH.

5. The method of claim 1, wherein the fluid is selected from the group consisting of M199, M199E serum, saline, Hartmann's solution, di-cation-free DPBS and effective mixtures thereof.

6. The method of claim 1, wherein the cell pellet is dislodged from at least one lobe of the inner bowl using an adjustable spray nozzle.

7. The method of claim 1, wherein fluid is added and removed from the bowl using at least one rotary coupling transport tube.

* * * * *